US011654145B2

(12) United States Patent
Deng et al.

(10) Patent No.: US 11,654,145 B2
(45) Date of Patent: May 23, 2023

(54) COMBINATION THERAPY INVOLVING DIARYL MACROCYCLIC COMPOUNDS

(71) Applicant: TURNING POINT THERAPEUTICS, INC., San Diego, CA (US)

(72) Inventors: Wei Deng, San Diego, CA (US); Dayong Zhai, San Diego, CA (US); Laura Rodon, San Diego, CA (US); Brion W. Murray, San Diego, CA (US); Jingrong J. Cui, San Diego, CA (US)

(73) Assignee: Turning Point Therapeutics, Inc., San Diego, CA (US)

( * ) Notice: Subject to any disclaimer, the term of this patent is extended or adjusted under 35 U.S.C. 154(b) by 129 days.

(21) Appl. No.: 17/104,752

(22) Filed: Nov. 25, 2020

(65) Prior Publication Data
US 2021/0220364 A1 Jul. 22, 2021

Related U.S. Application Data

(60) Provisional application No. 62/941,026, filed on Nov. 27, 2019, provisional application No. 62/981,822, filed on Feb. 26, 2020, provisional application No. 63/005,681, filed on Apr. 6, 2020.

(51) Int. Cl.
*A61K 31/519* (2006.01)
*A61P 35/00* (2006.01)
*A61K 31/517* (2006.01)

(52) U.S. Cl.
CPC .......... *A61K 31/519* (2013.01); *A61K 31/517* (2013.01); *A61P 35/00* (2018.01)

(58) Field of Classification Search
CPC .................................................. A61K 31/519
See application file for complete search history.

(56) References Cited

U.S. PATENT DOCUMENTS

| 2016/0166571 | A1 | 6/2016 | Janes et al. |
| 2018/0186813 | A1 | 7/2018 | Cui et al. |
| 2018/0194777 | A1 | 7/2018 | Cui et al. |
| 2018/0334454 | A1 | 11/2018 | Lanman et al. |
| 2019/0144444 | A1 | 5/2019 | Blake et al. |
| 2019/0270743 | A1 | 9/2019 | Marx et al. |

FOREIGN PATENT DOCUMENTS

| WO | 2015/112806 A2 | 7/2015 |
| WO | 2018/140554 A1 | 8/2018 |
| WO | 2020/055755 A1 | 3/2020 |

OTHER PUBLICATIONS

McMahon et al.(2000).*
Pinedo et al. (2000).*
International Search Report and Written Opinion received for PCT Application No. PCT/US2020/062390, dated Feb. 9, 2021, 8 pages.
Berge, S.M. et al. (Jan. 1977) "Pharmaceutical Salts", Journal of Pharmaceutical Sciences, 66(1):1-19.
Bromann, P.A. et al., (2004) "The Interplay between Src Family Kinases and Receptor Tyrosine Kinases", Oncogene, 23(48):7957-7968.
Brooks, G.D. et al. (2016) "IL6 Trans-signaling Promotes KRAS-Driven Lung Carcinogenesis", Cancer Research, 76(4):866-876.
Canon, J. et al. (Nov. 2019) "The Clinical KRAS(G12C) Inhibitor AMG 510 Drives Anti-Tumour Immunity", Nature, 575(7781):217-223 (26 pages).
Carvalho, P.D. et al. (Jan. 1, 2018) "KRAS Oncogenic Signaling Extends beyond Cancer Cells to Orchestrate the Microenvironment", Cancer Research, 78(1):7-14.
Carvalho, P.D. et al. (Dec. 13, 2019) "Targeting the Tumor Microenvironment: An Unexplored Strategy for Mutant KRAS Tumors", Cancers, Article No. 2010, 11(12): 15 pages.
Cullis et al. (Sep. 4, 2018) "Kras and Tumor Immunity: Friend or Foe?", Cold Spring Harbor Perspectives in Medicine, Article No. a031849, 8(9): 22 pages.
Golubovskaya, V.M. et al. (Aug. 2003) "Simultaneous Inhibition of Focal Adhesion Kinase and Src Enhances Detachment and Apoptosis in Colon Cancer Cell Lines", Molecular Cancer Research, 1(10):755-764.
Golubovskaya, V.M. et al. (Jul. 14, 2011) "Focal Adhesion Kinase and p53 Signal Transduction Pathways in Cancer," Frontiers in Bioscience, Author Manuscript, 15: 901-912 (18 pages).
Govindan, R. et al., (2019) "A Novel Molecule Targeting KRAS G12C Mutant Solid Tumors", Annals of Oncology, 30 (suppl 5): v159-v193, abstract only.
Hallin, J. et al. (Jan. 2020) "The KRAS G12C Inhibitor MRTX849 Provides Insight toward Therapeutic Susceptibility of KRAS Mutant Cancers in Mouse Models and Patients", Cancer Discovery, 10(1):54-71 (31 pages).
Hanahan, D. et al. (Mar. 4, 2011) "Hallmarks of Cancer: The Next Generation", Cell, 144(5):646-674.
Ianevski, A. et al., (Aug. 1, 2017) "SynergyFinder: A Web Application for Analyzing Drug Combination Dose-Response Matrix Data", Bioinformatics, 33(15):2413-2415.
Kanteti, R. et al. (May 24, 2016) "FAK And Paxillin, Two Potential Targets In Pancreatic Cancer", Oncotarget, 7(21):31586-31601.
Kelber, J.A. et al. (May 15, 2012) "KRas Induces a Sr/PEAK1/ErbB2 Kinase Amplification Loop That Drives Metastatic Growth and Therapy Resistance in Pancreatic Cancer", Cancer Research, 72(10):2554-2564.
Kessler, B.E. et al. (Apr. 2019) "Resistance to Src Inhibition Alters the BRAF-mutant Tumor Secretome to promote an Invasive Phenotype and Therapeutic Escape through a FAK>p130Cas>c-Jun Signaling Axis", Oncogene, 38(14):2565-2579 (26 pages).
Konstantinidou, G. et al. (Apr. 2013) "RHOA-FAK is a required Signaling Axis for the Maintenance of KRAS-driven Lung Adenocarcinomas", Cancer Discovery, 3(4):444-457 (22 pages).

(Continued)

*Primary Examiner* — Paul V Ward
(74) *Attorney, Agent, or Firm* — Mintz, Levin, Cohn, Ferris, Glovsky and Popeo, P.C.

(57) ABSTRACT

The present disclosure relates to methods and compositions for treating cancer with a diaryl macrocycle in combination with a KRAS inhibitor, such as an inhibitor of KRAS G12C.

30 Claims, 13 Drawing Sheets

(56) References Cited

OTHER PUBLICATIONS

Matsuo, Y. et al. (Jun. 2009) "K-Ras Promotes Angiogenesis Mediated by Immortalized Human Pancreatic Epithelial Cells through Mitogen-Activated Protein Kinase Signaling Pathways", Molecular Cancer Research, 7 (6):799-808 (19 pages).
Niu, G. et al. (Mar. 7, 2002) "Constitutive Stat3 Activity Up-regulates VEGF Expression and Tumor Angiogenesis", Oncogene, 21(13):2000-2008.
Ostrem, J.M. et al. (Nov. 28, 2013) "K-Ras(G12C) Inhibitors Allosterically Control GTP Affinity and Effector Interactions", Nature, 503(7477):548-551 (21 pages).
Rao, G. et al. (Aug. 2018) "Dasatinib Sensitises KRAS-Mutant Cancer Cells To Mitogen-Activated Protein Kinase Kinase Inhibitor Via Inhibition of TAZ Activity", European Journal of Cancer, 99:37-48.
Seguin, L. et al. (Apr. 2015) "Integrins and Cancer: Regulators of Cancer Stemness, Metastasis, and Drug Resistance", Trends in Cell Biology, 25(4):234-240 (17 pages).
Stolze, B. et al. (Feb. 23, 2015) "Comparative Analysis of KRAS Codon 12, 13, 18, 61, and 117 Mutations using Human MCF10A Isogenic Cell Lines", Scientific Reports, Article No. 8535, 5: 1-9 pages.
Tape, C.J. et al. (May 5, 2016) "Oncogenic KRAS Regulates Tumor Cell Signaling via Stromal Reciprocation", Cell, 165(4):910-920.
Van Maldegem, F. et al. (Jan. 14, 2020) "Mutant KRAS at the Heart of Tumor Immune Evasion", Immunity, 52 (1):14-16.
Van Nimwegen, M.J. et al. (Oct. 2006) "Focal Adhesion Kinase and Protein Kinase B Cooperate to Suppress Doxorubicin-Induced Apoptosis of Breast Tumor Cells", Molecular Pharmacology, 70(4):1330-1339.
Zaanan, A. et al. (Sep. 25, 2015) "The Mutant KRAS Gene Up-regulates BCL-XL Protein via STAT3 to Confer Apoptosis Resistance That Is Reversed by BIM Protein Induction and BCL-XL Antagonism", The Journal of Biological Chemistry, 290(39):23838-23849.
Zhang, S. et al. (2012)"Targeting Src Family Kinases in Anti-Cancer Therapies: Turning Promise into Triumph", Trends in Pharmacological Sciences, 33(3):122-128(14 pages).
Zhu, Z. et al. (Apr. 2014) "Inhibition of KRAS-driven Tumorigenicity by Interruption of an Autocrine Cytokine Circuit", Cancer Discovery, 4(4):452-465 (22 pages).

\* cited by examiner

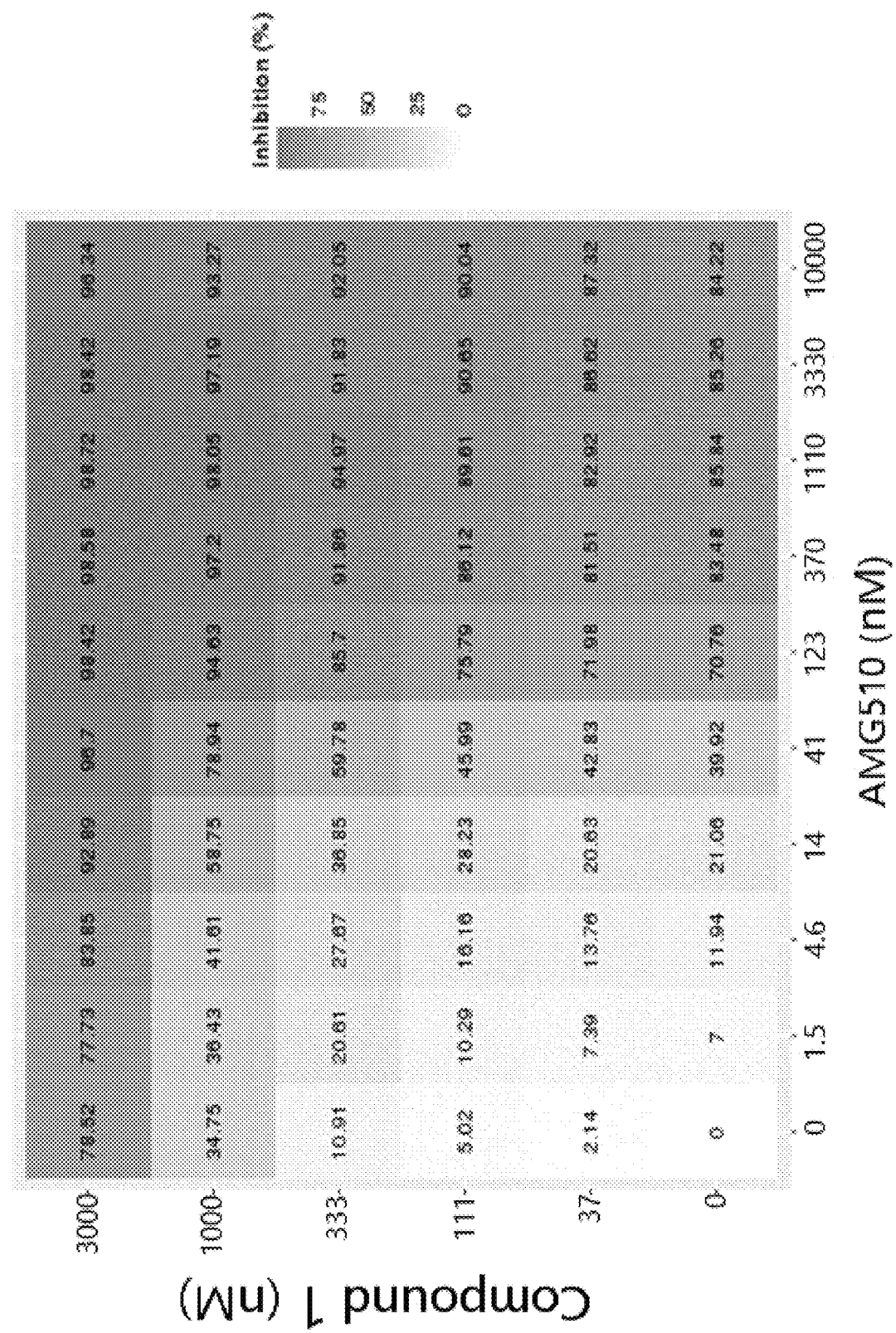

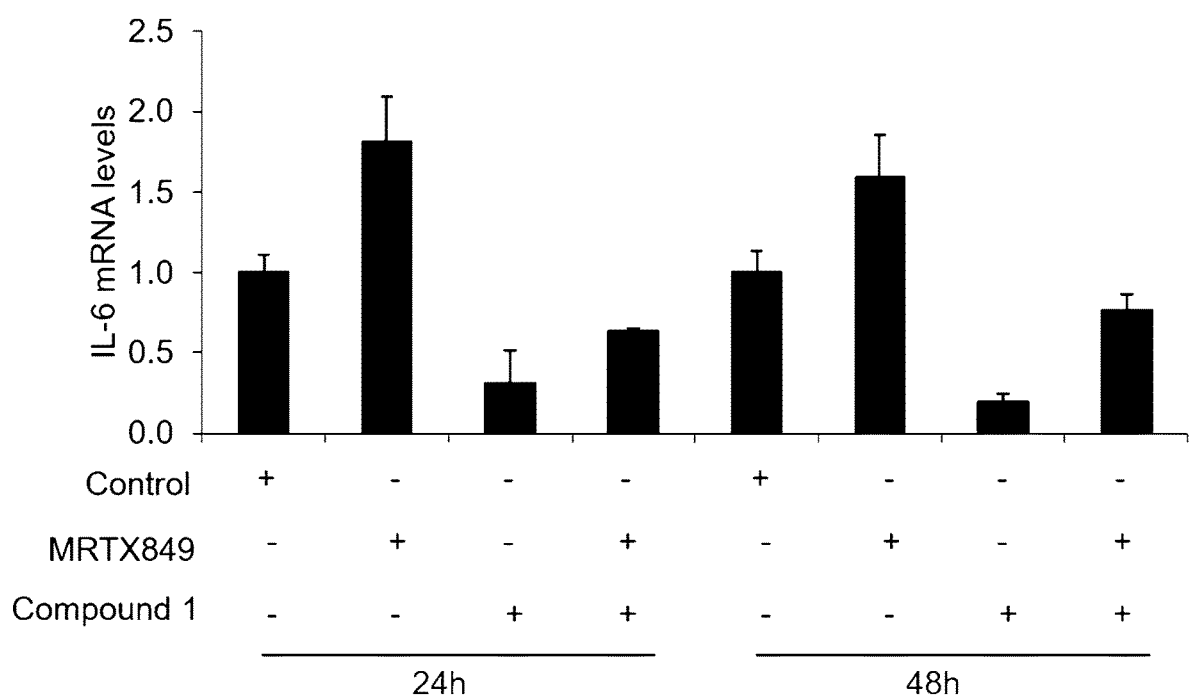

COMBINATION THERAPY INVOLVING DIARYL MACROCYCLIC COMPOUNDS

CROSS REFERENCES TO RELATED APPLICATIONS

This application claims priority to U.S. Provisional Application No. 62/941,026, filed Nov. 27, 2019; U.S. Provisional Application No. 62/981,822, filed Feb. 26, 2020; and U.S. Provisional Application No. 63/005,681, filed Apr. 6, 2020, each of which is incorporated herein in its entirety for all purposes.

TECHNICAL FIELD

The present disclosure relates to methods and compositions for treating cancer with a diaryl macrocycle in combination with a KRAS inhibitor, such as an inhibitor of KRAS G12C.

BACKGROUND

Kirsten Rat Sarcoma Viral Oncogene homolog KRAS is one of three RAS protein family members (N, H, and K-RAS) that are small membrane bound intracellular GTPase proteins. KRAS cycles between an inactive guanosine diphosphate (GDP)-bound state and an active guanosine triphosphate (GTP)-bound state. Active GTP-bound KRAS interacts with numerous effectors to stimulate multiple signaling pathways (e.g. PI3K-AKT-MTOR, RAF-MEK-ERK) to affect a range of cellular processes (e.g. survival, proliferation, cytoskeletal organization).

KRAS is one of the most frequently mutated oncogenes across a broad spectrum of human cancers (18%, Catalogue of Somatic Mutations in Cancer (COSMIC) database v90), including non-small cell lung, colorectal, pancreatic, uterine, bladder, stomach, renal, breast, skin, prostate, acute myeloid leukemia, cervical, liver acute lymphoblastic leukemia, ovarian, and brain cancers. KRAS mutations primarily occur in KRAS codons 12 and 13, and also occur in codons 18, 61, 117, and 146 at low frequencies and have distinct effects on tumor cell signaling based on the codon and missense mutation (Stolze et al. Sci Rep. 2015; 5:8535).

Direct targeting of a single KRAS mutation G12C through a covalent modality has produced a range of pre-clinical outcomes from insensitive to responsive in mouse tumor models that have the KRAS G12C mutation (Ostrem et al, Nature. 2013, 503(7477):548-51). Tumor regression has been reported in the treatment of patients with KRAS G12C mutated non-small cell lung cancer or colorectal cancer with KRAS G12C inhibitors AMG510 (Canon et al, Nature, 2019, 575, 217-223) and MRTX849 (Hallin et al, Cancer Discovery, 2020, 10(1) 54-71) in clinical studies. However, intrinsic and acquired resistance are expected to limit KRAS inhibitors used as a single agent in clinical application because of the development of signaling adaptation or selection of minor variants. KRAS G12C inhibitor MRTX849 demonstrated tumor regression in only 17 of 26 (65%) of KRAS G12C-positive cell line- and patient-derived mouse xenograft models from multiple tumor types and multiple resistance mechanisms including KRAS nucleotide cycling and feedback reactivation and/or bypass KRAS dependence limit the efficacy and duration of response of MRTX849 in non-clinical models (Hallin et al, Cancer Discovery, 2020, 10(1), 54-71). Covalent inhibitors of KRAS G12C have been reported to be more effective when combined with immune checkpoint inhibitory monoclonal antibodies such as those that block the programmed death-1 (PD-1) (Canon et al, Nature, 2019, 575, 217-223). Combinations that target MAPK pathway feedback re-activation, RTK-induced PI3K pathway activation, increased apoptosis, and suppress the proinflammatory tumor microenvironment will be necessary to provide significant improvements in clinical benefit.

Tumor cells reprogram the tumor microenvironment by many processes (e.g. immune suppression, induction of angiogenesis, altered metabolism) which are hallmarks of cancer (Hanahan and Weinberg, Cell 2011, 144(5), 646-674). Many studies show that oncogenic KRAS signaling induces the expression of a number of immunomodulatory factors such as TGFβ, GM-CSF, CXCL8, Interleukin-6 (IL-6), and IL-10 which interact with the tumor microenvironment to make it immune-suppressive (Cavalho et al Cancer Res 2018, 78(1), 7-14; Cullis et al., Cold Spring Harb. Perspect. Med 8, a031849; Maldegem and Downward, Immunity 2020, 52, 14-16). Mutant KRAS-driven cancer is known to reprogram the stroma to be pro-tumorigenic (Carvalho et al Cancers 2019, 11(12), 2010) and tumorigenicity is inhibited by interrupting autocrine cytokine signaling (Zhu et al., Cancer Discov 2014, 4, 452-65). One example is IL-6 secretion by mutant KRAS tumor cells. IL-6 is known to be upregulated in lung cancer and mediates signaling pathways that promote KRAS-driven lung tumorigenesis (Brooks et al., Cancer Res 2016. 76(4), 1-11). Mutant KRAS tumor cells secrete vascular endothelial growth factor (VEGF) and other angiogenic factors such as CXC chemokines to initiate angiogenesis is a paracrine process (Matsuo et al Mol Cancer Res 2009, 7(6), 799-808). Other paracrine processes remodel the stroma as well as alter tumor cell processes in addition to immune evasion and angiogenesis. For example, mutant KRAS cells can secrete insulin-like growth factor-1 which increases tumor cell mitochondrial capacity via IGF1R signaling (Tape et al., Cell 2016, 165(4), 910-920). As such, effective therapies for patients with cancers that have mutant KRAS will need to target the tumor cell as well as the tumor microenvironment.

SRC kinase has been identified to contribute broadly to cancer treatment resistance including radiotherapy, chemotherapy, and targeted therapy (Zhang S and Yu D. Trends Pharmacol Sci. 2012; 33(3): 122-8). SRC family kinases can promote mitogenic signaling from growth factor receptors in a number of ways, including initiation of signaling pathways required for DNA synthesis, control of receptor turnover, actin cytoskeleton rearrangements and motility, and survival (Bromann et al, Oncogene 2004; 23(48):7957-68). It was reported that KRAS induces a Src/PEAK1/ErbB2 kinase amplification loop that drives metastatic growth and therapy resistance in pancreatic cancer (Kelber et al, Cancer Res. 2012; 72(10):2554-64). The SRC inhibitor dasatinib was discovered to enhance the anti-tumor activity of MEK inhibitor through inhibition of TAZ activity and the combination of dasatinib and trametinib represents a potential strategy for the treatment of KRAS-driven cancers (Rao et al, Eur J Cancer. 2018 August; 99:37-48). FAK plays a vital role in signaling pathways mediated through integrins, RTKs, RAS, and TGFβ (Kanteti et al, Oncotarget. 2016; 7(21):31586-601) and is also likely to suppress p53 expression to promote cell survival (Golubovskaya et al, International Review of Cytology. 2007; 263:103-153). Recent findings have demonstrated that integrins participate in the regulation of cancer stem-cell biology and are required for cancer progression, metastasis, and drug resistance via SRC/FAK signaling (Seguin et al, Trends Cell Biol 2015; 25(4):

234-40). Src has been identified as a key mediator of thyroid cancer pro-tumorigenic processes and a promising therapeutic target for thyroid cancer.

Single-agent Src inhibition promotes a more invasive phenotype through an IL-1β>FAK>p130Cas>c-Jun>MMP signaling axis, and the combined inhibition of FAK and Src has the potential to block Src inhibitor-induced phenotype switch and resistance (Kessler et al, *Oncogene.* 2019; 38:2565-2579). Compensatory upregulation of the PI3K/AKT signaling pathway is a resistance mechanism in targeting KRAS mutation, which promotes cancer cell survival. FAK through phosphorylated Y397 directly interacts with the SH2 domain of p85, the regulatory subunit of PI3K to activate the PI3K pathway and suppress doxorubicin-induced apoptosis (van Nimwegen et al, *Mol Pharmacol.* 2006; 70(4): 1330-1339). Src mediated phosphorylation of FAK at Y925 creates a docking site for GRB2 which activates the small GTP protein RAS and the downstream ERK2 (MAPK) (Kanteti et al, Oncotarget. 2016; 7(21): 31586-601). Paxillin is a major component of focal adhesions that form a structural link between extracellular matrix and actin cytoskeleton. In cancer cells, its function is regulated through Src and FAK mediated phosphorylation. The dual inhibition of FAK and Src inhibitor was much more effective as compared to FAK inhibition alone as evidenced with increased cell detachment, inhibition of AKT/ERK1/2 and Src, and increased apoptosis (Golubovskaya et al, *Molecular Cancer Research.* 2003; 1(10):755-764). RhoA-FAK is a required signaling axis for the maintenance of KRAS-driven lung adenocarcinomas. Pharmacologic inhibition of FAK in vivo downregulates p-AKT and does not trigger the emergence of PI3K/AKT-dependent compensatory mechanisms (Konstantinidou et al, *Cancer Discov.* 2013, 3(4):444-57). KRAS G12C inhibitor AMG-510 are less effective in KRAS G12C mutant colon cancer than in NSCLC (Govindan et al, *Annals of Oncology,* 2019, 30 (suppl_5): v159-v193. 10.1093/annonc/mdz244). It was reported that mutant KRAS activated p-STAT3 (Tyr705) in the absence of IL-6 secretion, and BCL-XL up-regulation by STAT3 contributes to mutant KRAS-mediated apoptosis resistance in colon cancer (Zaanan et al, *J Biol Chem.* 2015; 290(39):23838-49). Therefore, inhibition of JAK2 leading to modulation of STAT3 phosphorylation can be used to enable a synergistic apoptotic response in KRAS mutant colon cancer as well as other mutant KRAS cancers. In addition, Src and FAK regulate STAT3 which controls the expression angiogenetic factors such as VEGF (Niu et al *Oncogene* 2002, 21(13), 2000-8) as well as a range of cytokines (Cavalho et al *Cancers* 2019, 11(12), 2010). Taken together, Src, FAK, and JAK2 have key roles in mutant KRAS cancer by enabling angiogenesis in tumors, creating a pro-tumor immune response in the tumor microenvironment, and facilitating tumor cell signaling—both tumor cell intrinsic and extrinsic. In addition, the combined inhibition of Src, FAK, and JAK2 would have additional utility in diseases that have a pro-inflammatory component such as asthma, inflammatory bowel disease, ulcerative colitis, Crohn's disease, and fibrosis.

Overall, direct pharmacological targeting of activated RAS proteins has been challenging and has not yet led to successful treatments in the clinic although early antitumor activities have been observed with KRAS G12C inhibitors AMG510 and MRTX849 in Phase 1 clinical studies in patients with KRAS G12C mutant cancers. The combination of a SRC/FAK/JAK2 inhibitor with an agent that inhibits KRAS G12C represents a novel therapeutic invention to maximize the antitumor activities and duration of response of an agent that inhibits KRAS G12C for the treatment of patients with the KRAS G12C mutation.

SUMMARY

It has been discovered that the combination of an agent that inhibits KRAS G12C and one or more compounds that inhibit FAK, SRC and/or JAK2 provides a robust response in cancers harboring a KRAS G12C mutation.

In one aspect, the disclosure provides a method for treating cancer in a host animal, the method comprising the step of administering to the host animal a therapeutically effective amount of one or more compounds that inhibit FAK, SRC and/or JAK2, in combination with a therapeutically effective amount of at least one agent that inhibits KRAS G12C. In some embodiments, the host animal is a human patient. In some embodiments, the host animal is a laboratory animal such as a rodent.

In another aspect, the disclosure provides a method for treating cancer in a host animal, the method comprising the step of administering to the host animal a therapeutically effective amount of a compound that inhibits FAK, SRC, and JAK2, in combination with a therapeutically effective amount of at least one agent that inhibits KRAS G12C. In some embodiments, the host animal is a human patient. In some embodiments, the host animal is a laboratory animal such as a rodent.

In another aspect, the disclosure provides one of more compounds that inhibit FAK, SRC and/or JAK2, or a pharmaceutically acceptable salt thereof, for use in the treatment of cancer in a patient, in combination with a therapeutically effective amount of at least one agent that inhibits KRAS G12C.

In another aspect, the disclosure provides a compound that inhibits FAK, SRC and JAK2, or a pharmaceutically acceptable salt thereof, for use in the treatment of cancer in a patient, in combination with a therapeutically effective amount of at least one agent that inhibits KRAS G12C.

In another aspect, the disclosure provides use of one or more compounds that inhibit FAK, SRC and/or JAK2, or a pharmaceutically acceptable salt thereof, in the preparation of a medicament comprising a therapeutically effective amount of the compound, for treating cancer in a patient in combination with a therapeutically effective amount of at least one agent that inhibits KRAS G12C.

In another aspect, the disclosure provides use of a compound that inhibits FAK, SRC and JAK2, or a pharmaceutically acceptable salt thereof, in the preparation of a medicament comprising a therapeutically effective amount of the compound, for treating cancer in a patient in combination with a therapeutically effective amount of at least one agent that inhibits KRAS G12C.

In another aspect, the disclosure provides a composition comprising one or more compounds that inhibit FAK, SRC and/or JAK2, or a pharmaceutically acceptable salt thereof, in a therapeutically effective amount, for use in the treatment of cancer in a patient, in combination with a therapeutically effective amount of at least one agent that inhibits KRAS G12C.

In another aspect, the disclosure provides a composition comprising a compound that inhibits FAK, SRC and JAK2, or a pharmaceutically acceptable salt thereof, in a therapeutically effective amount, for use in the treatment of cancer in a patient, in combination with a therapeutically effective amount of at least one agent that inhibits KRAS G12C.

In another aspect, the disclosure provides a medicament comprising one or more compounds that inhibit FAK, SRC and/or JAK2, or a pharmaceutically acceptable salt thereof, combined with an agent that inhibits KRAS G12C, or a pharmaceutically acceptable salt thereof, in fixed or free combination.

In another aspect, the disclosure provides a medicament comprising a compound that inhibits FAK, SRC and JAK2, or a pharmaceutically acceptable salt thereof, combined with an agent that inhibits KRAS G12C, or a pharmaceutically acceptable salt thereof, in fixed or free combination.

In another aspect, the disclosure provides a synergistic composition of one or more compounds that inhibit FAK, SRC and/or JAK2 and an agent that inhibits KRAS G12C, where the two components come into contact with each other at a locus.

In another aspect, the disclosure provides a synergistic composition of a compound that inhibits FAK, SRC and JAK2 and an agent that inhibits KRAS G12C, where the two components come into contact with each other at a locus.

In another aspect, the disclosure provides a synergistic composition of one or more compounds that inhibit FAK, SRC and/or JAK2, and an agent that inhibits KRAS G12C, where the two components come into contact with each other only in the human body.

In another aspect, the disclosure provides a synergistic composition of a compound that inhibits FAK, SRC and JAK2, and an agent that inhibits KRAS G12C, where the two components come into contact with each other only in the human body.

In some embodiments the compound that inhibits FAK, SRC and JAK2 is of the formula I

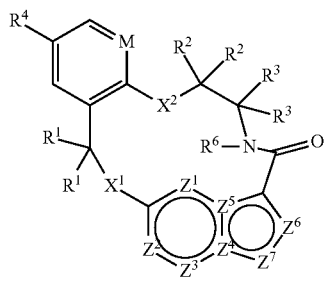

I wherein
M is $CR^5$ or N;
$X^1$ and $X^2$ are independently —$C(R^7)(R^8)$—, —S—, —S(O)—, —S(O)$_2$—, —O— or —N(R$^9$)—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-$C_6$ alkyl, —NH$_2$, —NH(C$_1$-$C_6$ alkyl), —N(C$_1$-$C_6$ alkyl)$_2$, —NHC(O)C$_1$-$C_6$ alkyl, —N(C$_1$-$C_6$ alkyl)C(O)C$_1$-$C_6$ alkyl, —NHC(O)NH$_2$, —NHC(O)NHC$_1$-$C_6$ alkyl, —N(C$_1$-$C_6$ alkyl)C(O)NH$_2$, —N(C$_1$-$C_6$ alkyl)C(O)NHC$_1$-$C_6$ alkyl, —NHC(O)N(C$_1$-$C_6$ alkyl)$_2$, —N(C$_1$-$C_6$ alkyl)C(O)N(C$_1$-$C_6$ alkyl)$_2$, —NHC(O)OC$_1$-$C_6$ alkyl, —N(C$_1$-$C_6$ alkyl)C(O)OC$_1$-$C_6$ alkyl, —NHS(O)(C$_1$-$C_6$ alkyl), —NHS(O)$_2$(C$_1$-$C_6$ alkyl), —N(C$_1$-$C_6$ alkyl)S(O)(C$_1$-$C_6$ alkyl), —N(C$_1$-$C_6$ alkyl)S(O)$_2$(C$_1$-$C_6$ alkyl), —NHS(O)NH$_2$, NHS(O)$_2$NH$_2$, —N(C$_1$-$C_6$ alkyl)S(O)NH$_2$, —N(C$_1$-$C_6$ alkyl)S(O)$_2$NH$_2$, —NHS(O)NH(C$_1$-$C_6$ alkyl), —NHS(O)$_2$NH(C$_1$-$C_6$ alkyl), —NHS(O)N(C$_1$-$C_6$ alkyl)$_2$, —NHS(O)$_2$N(C$_1$-$C_6$ alkyl)$_2$, —N(C$_1$-$C_6$ alkyl)S(O)NH(C$_1$-$C_6$ alkyl), —N(C$_1$-$C_6$ alkyl)S(O)$_2$NH(C$_1$-$C_6$ alkyl), —N(C$_1$-$C_6$ alkyl)S(O)N(C$_1$-$C_6$ alkyl)$_2$, —N(C$_1$-$C_6$ alkyl)S(O)$_2$N(C$_1$-$C_6$ alkyl)$_2$, —CO$_2$H, —C(O)OC$_1$-$C_6$ alkyl, —C(O)NH$_2$, —C(O)NH(C$_1$-$C_6$ alkyl), —C(O)N(C$_1$-$C_6$ alkyl)$_2$, —SC$_1$-$C_6$ alkyl, —S(O)C$_1$-$C_6$ alkyl, —S(O)$_2$C$_1$-$C_6$ alkyl, —S(O)NH(C$_1$-$C_6$ alkyl), —S(O)$_2$NH(C$_1$-$C_6$ alkyl), —S(O)N(C$_1$-$C_6$ alkyl)$_2$, —S(O)$_2$N(C$_1$-$C_6$ alkyl)$_2$, —P(C$_1$-$C_6$ alkyl)$_2$, —P(O)(C$_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-$C_6$ alkyl, —NH$_2$, —NH(C$_1$-$C_6$ alkyl), —N(C$_1$-$C_6$ alkyl)$_2$, NHC(O)C$_1$-$C_6$ alkyl, —N(C$_1$-$C_6$ alkyl)C(O)C$_1$-$C_6$ alkyl, —NHC(O)NH$_2$, —NHC(O)NHC$_1$-$C_6$ alkyl, —N(C$_1$-$C_6$ alkyl)C(O)NH$_2$, —N(C$_1$-$C_6$ alkyl)C(O)NHC$_1$-$C_6$ alkyl, —NHC(O)N(C$_1$-$C_6$ alkyl)$_2$, —N(C$_1$-$C_6$ alkyl)C(O)N(C$_1$-$C_6$ alkyl)$_2$, —NHC(O)OC$_1$-$C_6$ alkyl, —N(C$_1$-$C_6$ alkyl)C(O)OC$_1$-$C_6$ alkyl, —NHS(O)(C$_1$-$C_6$ alkyl), —NHS(O)$_2$(C$_1$-$C_6$ alkyl), —N(C$_1$-$C_6$ alkyl)S(O)(C$_1$-$C_6$ alkyl), —N(C$_1$-$C_6$ alkyl)S(O)$_2$(C$_1$-$C_6$ alkyl), —NHS(O)NH$_2$, NHS(O)$_2$NH$_2$, —N(C$_1$-$C_6$ alkyl)S(O)NH$_2$, —N(C$_1$-$C_6$ alkyl)S(O)$_2$NH$_2$, —NHS(O)NH(C$_1$-$C_6$ alkyl), —NHS(O)$_2$NH(C$_1$-$C_6$ alkyl), —NHS(O)N(C$_1$-$C_6$ alkyl)$_2$, —NHS(O)$_2$N(C$_1$-$C_6$ alkyl)$_2$, —N(C$_1$-$C_6$ alkyl)S(O)NH(C$_1$-$C_6$ alkyl), —N(C$_1$-$C_6$ alkyl)S(O)$_2$NH(C$_1$-$C_6$ alkyl), —N(C$_1$-$C_6$ alkyl)S(O)N(C$_1$-$C_6$ alkyl)$_2$, —N(C$_1$-$C_6$ alkyl)S(O)$_2$N(C$_1$-$C_6$ alkyl)$_2$, —CO$_2$H, —C(O)C$_1$-$C_6$ alkyl, —C(O)NH$_2$, —C(O)NH(C$_1$-$C_6$ alkyl), —C(O)N(C$_1$-$C_6$ alkyl)$_2$, —SC$_1$-$C_6$ alkyl, —S(O)C$_1$-$C_6$ alkyl, —S(O)$_2$C$_1$-$C_6$ alkyl, —S(O)NH(C$_1$-$C_6$ alkyl), —S(O)$_2$NH(C$_1$-$C_6$ alkyl), —S(O)N(C$_1$-$C_6$ alkyl)$_2$, —S(O)$_2$N(C$_1$-$C_6$ alkyl)$_2$, —P(C$_1$-$C_6$ alkyl)$_2$, —P(O)(C$_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —OC$_1$-$C_6$ alkyl, —NHC$_1$-$C_6$ alkyl, —N(C$_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —OC$_1$-$C_6$ alkyl, —NH$_2$, —NH(C$_1$-$C_6$ alkyl), —N(C$_1$-$C_6$ alkyl)$_2$, —CO$_2$H, —CO$_2$C$_1$-$C_6$ alkyl, —CONH$_2$, —CONH(C$_1$-$C_6$ alkyl), —CON(C$_1$-$C_6$ alkyl)$_2$, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —OC$_1$-$C_6$ alkyl, —NH$_2$, —NH(C$_1$-$C_6$ alkyl), —N(C$_1$-$C_6$ alkyl)$_2$, —NHC(O)C$_1$-$C_6$ alkyl, —N(C$_1$-$C_6$ alkyl)C(O)C$_1$-$C_6$ alkyl, —NHC(O)NH$_2$, —NHC(O)NHC$_1$-$C_6$ alkyl, —N(C$_1$-$C_6$ alkyl)C(O)NH$_2$, —N(C$_1$-$C_6$ alkyl)C(O)NHC$_1$-$C_6$ alkyl, —NHC(O)N(C$_1$-$C_6$ alkyl)$_2$, —N(C$_1$-$C_6$ alkyl)C(O)N(C$_1$-$C_6$ alkyl)$_2$, —NHC(O)OC$_1$-$C_6$ alkyl, —N(C$_1$-$C_6$ alkyl)C(O)OC$_1$-$C_6$ alkyl, —NHS(O)(C$_1$-$C_6$ alkyl), —NHS(O)$_2$(C$_1$-$C_6$ alkyl), —N(C$_1$-$C_6$ alkyl)S(O)(C$_1$-$C_6$ alkyl), —N(C$_1$-$C_6$ alkyl)S(O)$_2$(C$_1$-$C_6$ alkyl), —NHS(O)NH$_2$, NHS(O)$_2$NH$_2$, —N(C$_1$-$C_6$ alkyl)S(O)NH$_2$, —N(C$_1$-$C_6$ alkyl)S(O)$_2$NH$_2$, —NHS(O)NH(C$_1$-$C_6$ alkyl), —NHS(O)$_2$NH(C$_1$-$C_6$ alkyl), —NHS(O)N(C$_1$-$C_6$ alkyl)$_2$, —NHS(O)$_2$N(C$_1$-$C_6$ alkyl)$_2$, —N(C$_1$-$C_6$ alkyl)S(O)

NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —O$R^7$;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O—$C_1$-$C_6$ alkyl, —OH, —NH$_2$, —NH($C_1$-$C_6$ alkyl), —NH(phenyl), —NH(heteroaryl), —CN, or —CF$_3$, and provided that at least one of $Z^1$, $Z^2$, $Z^3$, $Z^4$, $Z^5$, $Z^6$ or $Z^7$ is N or NH;

or a pharmaceutically acceptable salt thereof.

In some embodiments of the above aspects, the compound that inhibits FAR, SRC and JAK2 is of the formula (referred to herein as Compound 1)

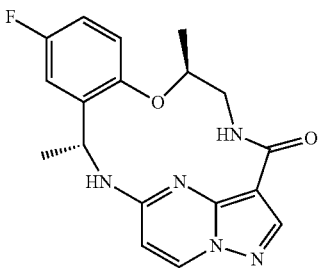 [SMILES: C[C@H]1CNC(=O)c2cnn3ccc(nc23)N[C@H](C)c2cc(F)ccc2O1]

or a pharmaceutically acceptable salt thereof.

In some embodiments of the above aspects, the at least one agent that inhibits KRAS G12C is a biological agent that inhibits KRAS G12C or a small molecule that inhibits KRAS G12C. In some embodiments of the above aspects, the at least one agent that inhibits KRAS G12C is a biological agent that inhibits KRAS G12C. In some embodiments of the above aspects, the at least one agent that inhibits KRAS G12C is a biological agent that inhibits KRAS G12C is an antibody, an antibody fragment, a peptide, an oligonucleotide, a ribonucleic acid, or an siRNA. In some embodiments of the above aspects, the at least one agent that inhibits KRAS G12C is a small molecule inhibitor.

Additional embodiments, features, and advantages of the disclosure will be apparent from the following detailed description and through practice of the disclosure. The compounds of the present disclosure can be described as embodiments in any of the following enumerated clauses.

It will be understood that any of the embodiments described herein can be used in connection with any other embodiments described herein to the extent that the embodiments do not contradict one another.

1. A method for treating cancer in a host animal, such as a human patient in need of such treatment, the method comprising the step of administering to the host animal a therapeutically effective amount of a compound that inhibits FAK, SRC, and JAK2, in combination with a therapeutically effective amount of at least one agent that inhibits KRAS G12C.

2. The method of clause 1, wherein the compound that inhibits FAK, SRC and JAK2 is of the formula I

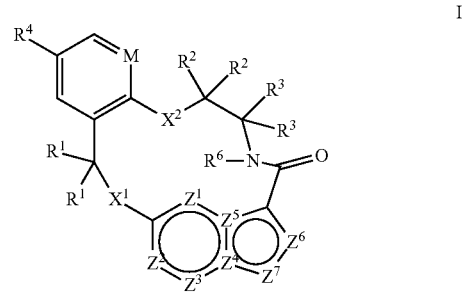

wherein

M is C$R^5$ or N;

$X^1$ and $X^2$ are independently —C($R^7$)($R^8$)—, —S—, —S(O)—, —S(O)$_2$—, —O— or —N($R^9$)—;

each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

3. The method of clause 1 or 2, wherein the compound that inhibits FAR, SRC and JAK2 is a compound of the formula

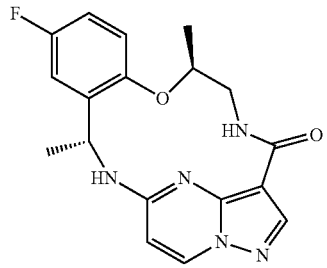 [SMILES: C[C@H]1CNC(=O)c2cnn3ccc(nc23)N[C@H](C)c2cc(F)ccc2O1]

or a pharmaceutically acceptable salt thereof.

4. The method of clause 1 to 3, wherein the cancer is selected from the group consisting of ALCL, non-small cell lung cancer, neuroblastoma, inflammatory myofibroblastic tumor, adult renal cell carcinoma, pediatric renal cell carcinoma, breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer, stomach cancer, and lung cancer.

5. The method of any one of clauses 1 to 4, wherein the cancer is non-small cell lung cancer, metastatic non-small cell lung cancer, colorectal cancer, metastatic colorectal cancer, pancreatic cancer, metastatic pancreatic cancer, uterine cancer, or metastatic uterine cancer.

6. The method of any one of clauses 1 to 5, wherein the cancer is non-small cell lung cancer.

7 The method of any one of clauses 1 to 5, wherein the cancer is colorectal cancer.

8. The method of any one of clauses 1 to 7, wherein the compound that inhibits FAK, SRC, and JAK2 is administered at the same time as, before, or after the at least one agent that inhibits KRAS G12C.

9. The method of any one of clauses 1 to 8, wherein IL-6 secretion from the cancer is deceased.

10. The method of any one of clauses 1 to 9, wherein the at least one agent that inhibits KRAS G12C is a biological agent that inhibits KRAS G12C or a small molecule inhibitor of KRAS G12C.

11. The method of any one of clauses 1 to 10, wherein the at least one agent that inhibits KRAS G12C is a biological agent that inhibits KRAS G12C.

12. The method of clause 11, wherein the biological agent that inhibits KRAS G12C is an antibody, an antibody fragment, a peptide, an oligonucleotide, a ribonucleic acid, or an siRNA.

13. The method of any one of clauses 1 to 10, wherein the at least one agent that inhibits KRAS G12C is a small molecule inhibitor of KRAS G12C.

14. The method of any one of clauses 1 to 10 or 13, wherein the at least one agent that inhibits KRAS G12C is AMG-510, MRTX849, JNJ-74699157, ARS-1620, MRTX1257, RM-007, or ADT-007.

15. The method of any one of clauses 1 to 10, 13 or 14, wherein the at least one agent that inhibits KRAS G12C is AMG-510, or a pharmaceutically acceptable salt thereof.

16. The method of any one of clauses 1 to 10, 13 or 14, wherein the at least one agent that inhibits KRAS G12C is MRTX849, or a pharmaceutically acceptable salt thereof.

17. The method according to any one of the preceding clauses, wherein the compound that inhibits FAK, SRC and JAK2 is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

18. The method according to any one of clauses 1 to 16, wherein the compound that inhibits FAK, SRC and JAK2 is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

19. The method according to any one of the preceding clauses, wherein the host animal is a human patient in need of such treatment who has not received a prior treatment.

20. The method according to any one of clauses 1 to 18, wherein the host animal is a human patient in need of such treatment who has received at least one prior treatment of one or more chemotherapeutic agents or immunotherapies.

21. The method according to any one of clauses 1 to 18 or 20, wherein the host animal is a human patient in need of such treatment who has received at least one prior treatment of one or more chemotherapeutic agents or immunotherapies, and developed an acquired resistance to the treatment, and/or developed bypass resistance to the treatment, and/or developed bypass resistance to the treatment regulated by FAK, SRC or JAK2.

22. A compound that inhibits FAK, SRC and JAK2, or a pharmaceutically acceptable salt thereof, for use in the treatment of cancer in a patient, in combination with a therapeutically effective amount of at least one agent that inhibits KRAS G12C.

23. The compound of clause 22, wherein the compound that inhibits FAK, SRC and JAK2 is of the formula I

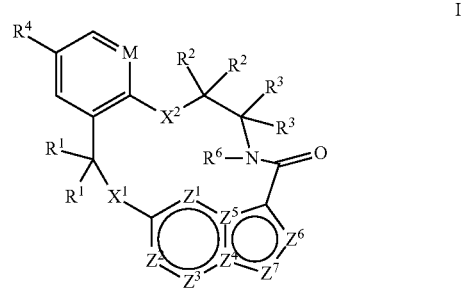

wherein

M is $CR^5$ or N;

$X^1$ and $X^2$ are independently —$C(R^7)(R^8)$—, —S—, —S(O)—, —S(O)$_2$—, —O— or —N($R^9$)—;

each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

24. The compound of clause 22 or 23, wherein the compound that inhibits FAR, SRC and JAK2 is a compound of the formula

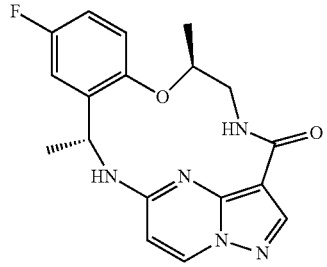

or a pharmaceutically acceptable salt thereof.

25. The compound of any one of clauses 22 to 24, wherein the cancer is selected from the group consisting of ALCL, non-small cell lung cancer, neuroblastoma, inflammatory myofibroblastic tumor, adult renal cell carcinoma, pediatric renal cell carcinoma, breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer, stomach cancer, and lung cancer.

26. The compound of any one of clauses 22 to 25, wherein the cancer is non-small cell lung cancer, metastatic non-small cell lung cancer, colorectal cancer, metastatic colorectal cancer, pancreatic cancer, metastatic pancreatic cancer, uterine cancer, or metastatic uterine cancer.

27. The compound of any one of clauses 22 to 26, wherein the cancer is non-small cell lung cancer.

28. The compound of any one of clauses 22 to 26, wherein the cancer is colorectal cancer.

29. The compound of any one of clauses 22 to 28, wherein the method comprises administering the compound that inhibits FAK, SRC, and JAK2 is administered at the same time as, before, or after the at least one agent that inhibits KRAS G12C.

30. The compound of any one of clauses 22 to 29, wherein IL-6 secretion from the cancer is deceased.

31. The compound of any one of clauses 22 to 30, the at least one agent that inhibits KRAS G12C is a biological agent that inhibits KRAS G12C or a small molecule inhibitor of KRAS G12C.

32. The compound of any one of clauses 22 to 31, wherein the at least one agent that inhibits KRAS G12C is a biological agent that inhibits KRAS G12C.

33. The compound of clause 32, wherein the biological agent that inhibits KRAS G12C is an antibody, an antibody fragment, a peptide, an oligonucleotide, a ribonucleic acid, or an siRNA.

34. The compound of any one of clauses 22 to 31, wherein the at least one agent that inhibits KRAS G12C is a small molecule inhibitor of KRAS G12C.

35 The compound of any one of clauses 22 to 31 or 34, wherein the at least one agent that inhibits KRAS G12C is AMG-510, MRTX849, JNJ-74699157, ARS-1620, MRTX1257, RM-007, or ADT-007.

36. The compound of any one of clauses 22 to 31, 34, or 35, wherein the at least one agent that inhibits KRAS G12C is AMG-510, or a pharmaceutically acceptable salt thereof.

37. The compound of any one of clauses 22 to 31, 34, or 35, wherein the at least one agent that inhibits KRAS G12C is MRTX849, or a pharmaceutically acceptable salt thereof.

38. The compound according to any one of clauses 22 to 37, wherein the compound that inhibits FAK, SRC and JAK2 is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

39. The compound according to any one of clauses 22 to 37, wherein the compound that inhibits FAK, SRC and JAK2 is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

40. The compound according to any one of clauses 22 to 39, wherein the patient has not received a prior treatment.

41. The compound according to any one of clauses 22 to 39, wherein the patient has received at least one prior treatment of one or more chemotherapeutic agents or immunotherapies.

42. The compound according to any one of clauses 22 to 39, wherein the patient has received at least one prior treatment of one or more chemotherapeutic agents or immunotherapies, and developed an acquired resistance to the treatment, and/or developed bypass resistance to the treatment, and/or developed bypass resistance to the treatment regulated by FAK, SRC or JAK2.

43. Use of a compound that inhibits FAK, SRC and JAK2, or a pharmaceutically acceptable salt thereof, in the preparation of a medicament comprising a therapeutically effective amount of the compound, for treating cancer in a patient in combination with a therapeutically effective amount of at least one agent that inhibits KRAS G12C.

44. The use of clause 43, wherein the compound that inhibits FAK, SRC and JAK2 is of the formula I

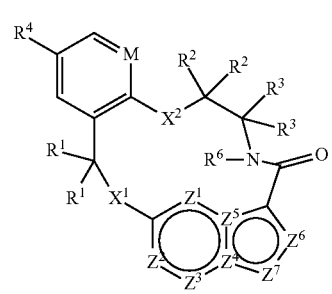

wherein
M is $CR^5$ or N;
$X^1$ and $X^2$ are independently —$C(R^7)(R^8)$—, —S—, —S(O)—, —S(O)$_2$—, —O— or —N($R^9$)—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

45. The use of clause 43 or 44, wherein the compound that inhibits FAR, SRC and JAK2 is a compound of the formula

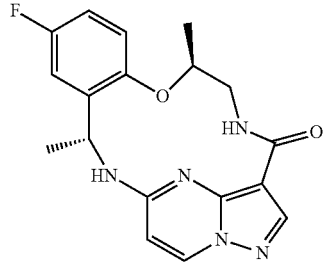 [SMILES: C[C@H]1CNC(=O)c2cnn3ccc(nc23)N[C@H](C)c2cc(F)ccc2O1]

or a pharmaceutically acceptable salt thereof.

46. The use of any one of clauses 43 to 45, wherein the cancer is selected from the group consisting of ALCL, non-small cell lung cancer, neuroblastoma, inflammatory myofibroblastic tumor, adult renal cell carcinoma, pediatric renal cell carcinoma, breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer, stomach cancer, and lung cancer.

47. The use of any one of clauses 43 to 46, wherein the cancer is non-small cell lung cancer, metastatic non-small cell lung cancer, colorectal cancer, metastatic colorectal cancer, pancreatic cancer, metastatic pancreatic cancer, uterine cancer, or metastatic uterine cancer.

48. The use of any one of clauses 43 to 46, wherein the cancer is non-small cell lung cancer.

49. The use of any one of clauses 43 to 46, wherein the cancer is colorectal cancer.

50. The use of any one of clauses 43 to 49, wherein the medicament comprising the compound that inhibits FAK, SRC, and JAK2 is administered to the patient at the same time as, before, or after the at least one agent that inhibits KRAS G12C.

51. The use of any one of clauses 43 to 50, wherein IL-6 secretion from the cancer is deceased.

52. The use of any one of clauses 43 to 51, wherein the at least one agent that inhibits KRAS G12C is a biological agent that inhibits KRAS G12C or a small molecule inhibitor of KRAS G12C.

53. The use of any one of clauses 43 to 52, wherein the at least one agent that inhibits KRAS G12C is a biological agent that inhibits KRAS G12C.

54. The use of any one of clauses 43 to 53, wherein the biological agent that inhibits KRAS G12C is an antibody, an antibody fragment, a peptide, an oligonucleotide, a ribonucleic acid, or an siRNA.

55. The use of any one of clauses 43 to 52, wherein the at least one agent that inhibits KRAS G12C is a small molecule inhibitor of KRAS G12C.

56. The use of any one of clauses 43 to 52 or 55, wherein the at least one agent that inhibits KRAS G12C is AMG-510, MRTX849, JNJ-74699157, ARS-1620, MRTX1257, RM-007, or ADT-007.

57. The use of any one of clauses 43 to 52, 55, or 56, wherein the at least one agent that inhibits KRAS G12C is AMG-510, or a pharmaceutically acceptable salt thereof.

58. The use of any one of clauses 43 to 52, 55, or 56, wherein the at least one agent that inhibits KRAS G12C is MRTX849, or a pharmaceutically acceptable salt thereof.

59. The use of any one of clauses 43 to 58, wherein the compound that inhibits FAK, SRC and JAK2 is provided in the medicament in an amount of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is provided in an amount of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

60. The use of any one of clauses 43 to 58, wherein the compound that inhibits FAK, SRC and JAK2 is provided in the medicament in an amount of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is provided in an amount of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

61. The use of any one of clauses 43 to 60, wherein the patient has not received a prior treatment.

62. The use of any one of clauses 43 to 60, wherein the patient has received at least one prior treatment of one or more chemotherapeutic agents or immunotherapies.

63. The use of any one of clauses 43 to 60 or 62, wherein the patient has received at least one prior treatment of one or more chemotherapeutic agents or immunotherapies, and developed an acquired resistance to the treatment, and/or developed bypass resistance to the treatment, and/or developed bypass resistance to the treatment regulated by FAK, SRC or JAK2.

64. A composition comprising a compound that inhibits FAK, SRC and JAK2, or a pharmaceutically acceptable salt thereof, in a therapeutically effective amount, for use in the treatment of cancer in a patient, in combination with a therapeutically effective amount of at least one agent that inhibits KRAS G12C.

65. The composition of clause 64, wherein the compound that inhibits FAK, SRC and JAK2 is of the formula I

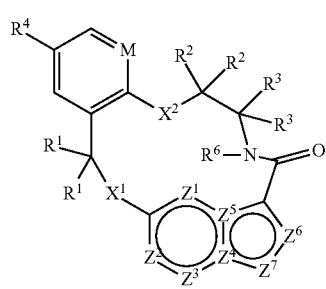

wherein

M is $CR^5$ or N;

$X^1$ and $X^2$ are independently —C($R^7$)($R^8$)—, —S—, —S(O)—, —S(O)$_2$—, —O— or —N($R^9$)—;

each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N(C₁-C₆ alkyl)S(O)(C₁-C₆ alkyl), —N(C₁-C₆ alkyl)S(O)₂(C₁-C₆ alkyl), —NHS(O)NH₂, NHS(O)₂NH₂, —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —NHS(O)N(C₁-C₆ alkyl)₂, —NHS(O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, —C(O)C₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —P(C₁-C₆ alkyl)₂, —P(O)(C₁-C₆ alkyl)₂, C₃-C₆ cycloalkyl, or 3- to 7-membered heterocycloalkyl;

R⁴ and R⁵ are each independently H, fluoro, chloro, bromo, C₁-C₆ alkyl, —OH, —CN, —OC₁-C₆ alkyl, —NHC₁-C₆ alkyl, —N(C₁-C₆ alkyl)₂ or —CF₃;

R⁶ is H, C₁-C₆ alkyl or 3- to 7-membered heterocycloalkyl, wherein each hydrogen atom in C₁-C₆ alkyl or 3- to 7-membered heterocycloalkyl is independently optionally substituted by halogen, —OH, —CN, —OC₁-C₆ alkyl, —NH₂, —NH(C₁-C₆ alkyl), —N(C₁-C₆ alkyl)₂, —CO₂H, —CO₂C₁-C₆ alkyl, —CONH₂, —CONH(C₁-C₆ alkyl), —CON(C₁-C₆ alkyl)₂, C₃-C₆ cycloalkyl, or 3- to 7-membered heterocycloalkyl;

each R⁷ and R⁸ is independently H, deuterium, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl or 5- to 7-membered heteroaryl; wherein each hydrogen atom in C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, or 5- to 7-membered heteroaryl is independently optionally substituted by deuterium, halogen, —OH, —CN, —OC₁-C₆ alkyl, —NH₂, —NH(C₁-C₆ alkyl), —N(C₁-C₆ alkyl)₂, —NHC(O)C₁-C₆ alkyl, —N(C₁-C₆ alkyl)C(O)C₁-C₆ alkyl, —NHC(O)NH₂, —NHC(O)NHC₁-C₆ alkyl, —N(C₁-C₆ alkyl)C(O)NH₂, —N(C₁-C₆ alkyl)C(O)NHC₁-C₆ alkyl, —NHC(O)N(C₁-C₆ alkyl)₂, —N(C₁-C₆ alkyl)C(O)N(C₁-C₆ alkyl)₂, —NHC(O)OC₁-C₆ alkyl, —N(C₁-C₆ alkyl)C(O)OC₁-C₆ alkyl, —NHS(O)(C₁-C₆ alkyl), —NHS(O)₂(C₁-C₆ alkyl), —N(C₁-C₆ alkyl)S(O)(C₁-C₆ alkyl), —N(C₁-C₆ alkyl)S(O)₂(C₁-C₆ alkyl), —NHS(O)NH₂, NHS(O)₂NH₂, —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —NHS(O)N(C₁-C₆ alkyl)₂, —NHS(O)₂N(C₁-C₆ alkyl)₂, —N(C₁-C₆ alkyl)S(O) NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —P(C₁-C₆ alkyl)₂, —P(O)(C₁-C₆ alkyl)₂, C₃-C₆ cycloalkyl, or 3- to 7-membered heterocycloalkyl;

each R⁹ is independently H, deuterium, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, or mono- or bicyclic heteroaryl; wherein each hydrogen atom in C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, or 5- to 7-membered heteroaryl is independently optionally substituted by deuterium, halogen, C₁-C₆ alkyl, C₁-C₆ haloalkyl or —OR⁷;

each $Z^1$, $Z^2$, $Z^3$, $Z^4$, $Z^5$, $Z^6$ or $Z^7$ is independently N, NH, or C(R¹⁰), wherein each R¹⁰ is independently H, deuterium, halogen, C₁-C₆ alkyl, —O—C₁-C₆ alkyl, —OH, —NH₂, —NH(C₁-C₆ alkyl), —NH(phenyl), —NH(heteroaryl), —CN, or —CF₃, and provided that at least one of $Z^1$, $Z^2$, $Z^3$, $Z^4$, $Z^5$, $Z^6$ or $Z^7$ is N or NH;

or a pharmaceutically acceptable salt thereof.

66. The composition of clause 64 or 65, wherein the compound that inhibits FAR, SRC and JAK2 is a compound of the formula

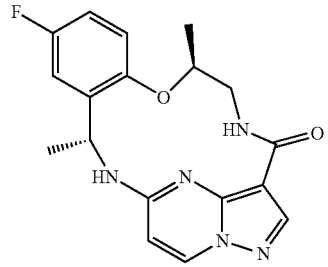 [SMILES: C[C@H]1CNC(=O)c2cnn3ccc(nc23)N[C@H](C)c2cc(F)ccc2O1]

or a pharmaceutically acceptable salt thereof.

67. The composition of any one of clauses 64 to 66, wherein the cancer is selected from the group consisting of ALCL, non-small cell lung cancer, neuroblastoma, inflammatory myofibroblastic tumor, adult renal cell carcinoma, pediatric renal cell carcinoma, breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer, stomach cancer, and lung cancer.

68. The composition of any one of clauses 64 to 67, wherein the cancer is non-small cell lung cancer, metastatic non-small cell lung cancer, colorectal cancer, metastatic colorectal cancer, pancreatic cancer, metastatic pancreatic cancer, uterine cancer, or metastatic uterine cancer.

69. The composition of any one of clauses 64 to 68, wherein the cancer is non-small cell lung cancer.

70. The composition of any one of clauses 64 to 68, wherein the cancer is colorectal cancer.

71. The composition of any one of clauses 64 to 70, wherein the composition comprising the compound that inhibits FAK, SRC, and JAK2 is administered to the patient at the same time as, before, or after the at least one agent that inhibits KRAS G12C.

72. The composition of any one of clauses 64 to 71, wherein IL-6 secretion from the cancer is deceased.

73. The composition of any one of clauses 64 to 72, wherein the at least one agent that inhibits KRAS G12C is a biological agent that inhibits KRAS G12C or a small molecule inhibitor of KRAS G12C.

74. The composition of any one of clauses 64 to 73, wherein the at least one agent that inhibits KRAS G12C is a biological agent that inhibits KRAS G12C.

75. The composition of clause 74, wherein the biological agent that inhibits KRAS G12C is an antibody, an antibody fragment, a peptide, an oligonucleotide, a ribonucleic acid, or an siRNA.

76. The composition of any one of clauses 64 to 73, wherein the at least one agent that inhibits KRAS G12C is a small molecule inhibitor of KRAS G12C.

77. The composition of any one of clauses 64 to 73 or 76, wherein the at least one agent that inhibits KRAS G12C is AMG-510, MRTX849, JNJ-74699157, ARS-1620, MRTX1257, RM-007, or ADT-007.

78. The composition of any one of clauses 64 to 73, 76, or 77, wherein the at least one agent that inhibits KRAS G12C is AMG-510, or a pharmaceutically acceptable salt thereof.

79. The composition of any one of clauses 64 to 73, 76, or 77, wherein the at least one agent that inhibits KRAS G12C is MRTX849, or a pharmaceutically acceptable salt thereof.

80. The composition of any one of clauses 64 to 79, wherein the compound that inhibits FAK, SRC and JAK2 is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

81. The composition of any one of clauses 64 to 79, wherein the compound that inhibits FAK, SRC and JAK2 is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

82. The composition of any one of clauses 64 to 81, wherein the host animal is a human patient in need of such treatment who has not received a prior treatment.

83. The composition of any one of clauses 64 to 81, wherein the host animal is a human patient in need of such treatment who has received at least one prior treatment of one or more chemotherapeutic agents or immunotherapies.

84. The composition of any one of clauses 64 to 81 or 83, wherein the host animal is a human patient in need of such treatment who has received at least one prior treatment of one or more chemotherapeutic agents or immunotherapies, and/or developed an acquired resistance to the treatment, or developed bypass resistance to the treatment, and/or developed bypass resistance to the treatment regulated by FAK, SRC or JAK2.

85. A medicament comprising a compound that inhibits FAK, SRC and JAK2, or a pharmaceutically acceptable salt thereof, combined with at least one agent that inhibits KRAS G12C, in fixed or free combination.

86. The medicament of clause 85, wherein the compound that inhibits FAK, SRC and JAK2 is of the formula I

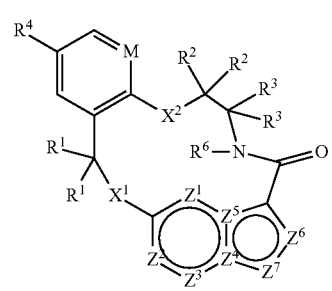

wherein
M is $CR^5$ or N;
$X^1$ and $X^2$ are independently —$C(R^7)(R^8)$—, —S—, —S(O)—, —S(O)$_2$—, —O— or —$N(R^9)$—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$C(O)OR^7$ or —$C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, $NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)C_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$C(O)OR^7$ or —$C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, $NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O) OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S (O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$ N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O) OC$_1$-C$_6$ alkyl, —N(C$_1$-C$_6$ alkyl)C(O)OC$_1$-C$_6$ alkyl, —NHS (O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S (O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O) NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S (O)$_2$N(C$_1$-C$_6$ alkyl)$_2$, —CO$_2$H, —C(O)C$_1$-C$_6$ alkyl, —C(O) NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O) N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

87. The medicament of clause 85 or 86, wherein the compound that inhibits FAR, SRC and JAK2 is a compound of the formula

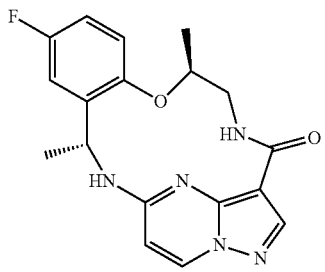 [SMILES: C[C@H]1CNC(=O)c2cnn3ccc(nc23)N[C@H](C)c2cc(F)ccc2O1]

or a pharmaceutically acceptable salt thereof.

88. The medicament of any one of clauses 85 to 87, wherein medicament provides a synergistic effect on a cancer selected from the group consisting of wherein the cancer is selected from the group consisting of ALCL, non-small cell lung cancer, neuroblastoma, inflammatory myofibroblastic tumor, adult renal cell carcinoma, pediatric renal cell carcinoma, breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer, stomach cancer, and lung cancer.

89. The medicament of any one of clauses 85 to 88, wherein the cancer is non-small cell lung cancer, metastatic non-small cell lung cancer, colorectal cancer, metastatic colorectal cancer, pancreatic cancer, metastatic pancreatic cancer, uterine cancer, or metastatic uterine cancer.

90. The medicament of any one of clauses 85 to 89, wherein the cancer is non-small cell lung cancer.

91. The medicament of any one of clauses 85 to 89, wherein the cancer is colorectal cancer.

92. The medicament of any one of clauses 85 to 89, wherein the cancer is pancreatic cancer.

93. The medicament of any one of clauses 85 to 92, wherein IL-6 secretion from the cancer is deceased.

94. The medicament of any one of clauses 85 to 93, wherein the at least one agent that inhibits KRAS G12C is a biological agent that inhibits KRAS G12C or a small molecule inhibitor of KRAS G12C.

95. The medicament of any one of clauses 85 to 94, wherein the at least one agent that inhibits KRAS G12C is a biological agent that inhibits KRAS G12C.

96. The medicament of clause 95, wherein the biological agent that inhibits KRAS G12C is an antibody, an antibody fragment, a peptide, an oligonucleotide, a ribonucleic acid, or an siRNA.

97. The medicament of any one of clauses 85 to 95, wherein the at least one agent that inhibits KRAS G12C is a small molecule inhibitor of KRAS G12C.

98. The medicament of any one of clauses 85 to 95 or 97, wherein the at least one agent that inhibits KRAS G12C is AMG-510, MRTX849, JNJ-74699157, ARS-1620, MRTX1257, RM-007, or ADT-007.

99. The medicament of any one of clauses 85 to 95, 97 or 99, wherein the at least one agent that inhibits KRAS G12C is AMG-510, or a pharmaceutically acceptable salt thereof.

100. The medicament of any one of clauses 85 to 95, 97 or 99, wherein the at least one agent that inhibits KRAS G12C is MRTX849, or a pharmaceutically acceptable salt thereof.

101. The medicament of any one of clauses 85 to 100, wherein the compound that inhibits FAK, SRC and JAK2 is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

102. The medicament of any one of clauses 85 to 100, wherein the compound that inhibits FAK, SRC and JAK2 is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

103. A synergistic composition of a compound that inhibits FAK, SRC and JAK2 and an agent that inhibits KRAS G12C, where the two components come into contact with each other at a locus.

104. The synergistic composition of clause 103, wherein the compound that inhibits FAK, SRC and JAK2 is of the formula I

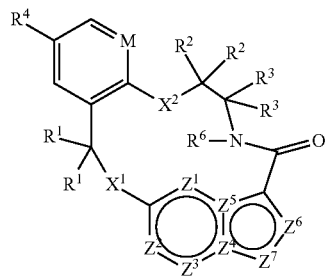

wherein
M is $CR^5$ or N;
$X^1$ and $X^2$ are independently —$C(R^7)(R^8)$—, —S—, —S(O)—, —S(O)$_2$—, —O— or —$N(R^9)$—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$C(O)OR^7$ or —$C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, $NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)C_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, $C_3$-$C_6$ cycloalkyl, or 3- to 7-membered heterocycloalkyl;
each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$C(O)OR^7$ or —$C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, $NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, $NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)C_1$-$C_6$ alkyl, —$C(O)NH_2$, —$C(O)NH(C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —CO$_2$$C_1$-$C_6$ alkyl, —CONH$_2$, —CONH($C_1$-$C_6$ alkyl), —CON($C_1$-$C_6$ alkyl)$_2$, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —OR$^7$;

each $Z^1$, $Z^2$, $Z^3$, $Z^4$, $Z^5$, $Z^6$ or $Z^7$ is independently N, NH, or C(R$^{10}$), wherein each R$^{10}$ is independently H, deuterium, halogen, $C_1$-$C_6$ alkyl, —O—$C_1$-$C_6$ alkyl, —OH, —NH$_2$, —NH($C_1$-$C_6$ alkyl), —NH(phenyl), —NH(heteroaryl), —CN, or —CF$_3$, and provided that at least one of $Z^1$, $Z^2$, $Z^3$, $Z^4$, $Z^5$, $Z^6$ or $Z^7$ is N or NH;

or a pharmaceutically acceptable salt thereof.

105. The synergistic composition of clause 103 or 104, wherein the compound that inhibits FAR, SRC and JAK2 is a compound of the formula

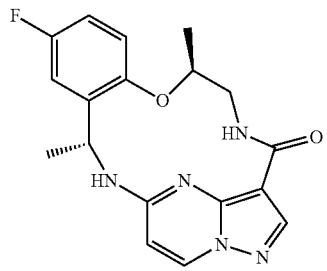 [SMILES: C[C@H]1CNC(=O)c2cnn3ccc(nc23)N[C@H](C)c2cc(F)ccc2O1]

or a pharmaceutically acceptable salt thereof.

106. The synergistic composition of any one of clauses 103 to 105, wherein the locus is a cancer or a cancer cell.

107. The synergistic composition of any one of clauses 103 to 106, wherein the locus is a cancer selected from the group consisting of ALCL, non-small cell lung cancer, neuroblastoma, inflammatory myofibroblastic tumor, adult renal cell carcinoma, pediatric renal cell carcinoma, breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer, stomach cancer, and lung cancer.

108. The synergistic composition of clause 107, wherein the cancer is non-small cell lung cancer, metastatic non-small cell lung cancer, colorectal cancer, metastatic colorectal cancer, pancreatic cancer, metastatic pancreatic cancer, uterine cancer, or metastatic uterine cancer.

109. The synergistic composition of clause 107, wherein the cancer is non-small cell lung cancer.

110. The synergistic composition of clause 107, wherein the cancer is colorectal cancer.

111. The synergistic composition of clause 107, wherein the cancer is pancreatic cancer.

112. The synergistic composition of any one of clauses 106 to 111, wherein IL-6 secretion from the cancer is deceased.

113. The synergistic composition of any one of clauses 103 to 112, wherein the agent that inhibits KRAS G12C is a biological agent that inhibits KRAS G12C or a small molecule inhibitor of KRAS G12C.

114. The synergistic composition of any one of clauses 103 to 113, wherein the agent that inhibits KRAS G12C is a biological agent that inhibits KRAS G12C.

115. The synergistic composition of clause 114, wherein the biological agent that inhibits KRAS G12C is an antibody, an antibody fragment, a peptide, an oligonucleotide, a ribonucleic acid, or an siRNA.

116. The synergistic composition of any one of clauses 103 to 112, wherein the at least one agent that inhibits KRAS G12C is a small molecule inhibitor of KRAS G12C.

117 The synergistic composition of any one of clauses 103 to 112 or 116, wherein the at least one agent that inhibits KRAS G12C is AMG-510, MRTX849, JNJ-74699157, ARS-1620, MRTX1257, RM-007, or ADT-007.

118. The synergistic composition of any one of clauses 103 to 112, 116, or 117 wherein the at least one agent that inhibits KRAS G12C is AMG-510, or a pharmaceutically acceptable salt thereof.

119. The synergistic composition of any one of clauses 103 to 112, 116, or 117, wherein the at least one agent that inhibits KRAS G12C is MRTX849, or a pharmaceutically acceptable salt thereof.

120. The synergistic composition of any one of clauses 103 to 119, wherein the compound that inhibits FAK, SRC and JAK2 is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

121. The synergistic composition of any one of clauses 103 to 119, wherein the compound that inhibits FAK, SRC and JAK2 is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

122. The synergistic composition of any one of clauses 106 to 119, wherein the cancer or cancer cell has previously been contacted with at least one prior treatment of one or more chemotherapeutic agents or immunotherapies.

123. The synergistic composition of any one of clauses 106 to 119, wherein the cancer or cancer cell has previously been contacted with at least one prior treatment of one or more chemotherapeutic agents or immunotherapies, and/or developed an acquired resistance to the treatment, or developed bypass resistance to the treatment, and/or developed bypass resistance to the treatment regulated by FAK, SRC or JAK2.

124. A synergistic composition of a compound that inhibits FAK, SRC and JAK2 and an agent that inhibits KRAS G12C, where the two components come into contact with each other only in the human body.

125. The synergistic composition of clause 124, wherein the compound that inhibits FAK, SRC and JAK2 is of the formula I

I wherein
M is $CR^5$ or N;
$X^1$ and $X^2$ are independently —C($R^7$)($R^8$)—, —S—, —S(O)—, —S(O)$_2$—, —O— or —N($R^9$)—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

126. The synergistic composition of clause 124 or 125, wherein the compound that inhibits FAR, SRC and JAK2 is a compound of the formula

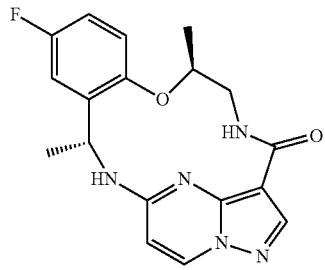 [SMILES: C[C@H]1CNC(=O)c2cnn3ccc(nc23)N[C@H](C)c2cc(F)ccc2O1]

or a pharmaceutically acceptable salt thereof.

127. The synergistic composition of any one of clauses 124 to 126, wherein the agent that inhibits KRAS G12C is a biological agent that inhibits KRAS G12C or a small molecule inhibitor of KRAS G12C.

128. The synergistic composition of any one of clauses 124 to 127, wherein the agent that inhibits KRAS G12C is a biological agent that inhibits KRAS G12C.

129. The synergistic composition of clause 128, wherein the biological agent that inhibits KRAS G12C is an antibody, an antibody fragment, a peptide, an oligonucleotide, a ribonucleic acid, or an siRNA.

130. The synergistic composition of any one of clauses 124 to 128, wherein the at least one agent that inhibits KRAS G12C is a small molecule inhibitor of KRAS G12C.

131. The synergistic composition of any one of clauses 124 to 128 or 130, wherein the at least one agent that inhibits KRAS G12C is AMG-510, MRTX849, JNJ-74699157, ARS-1620, MRTX1257, RM-007, or ADT-007.

132. The synergistic composition of any one of clauses 124 to 128, 130 or 131, wherein the at least one agent that inhibits KRAS G12C is AMG-510, or a pharmaceutically acceptable salt thereof.

133. The synergistic composition of any one of clauses 124 to 128, 130 or 131, wherein the at least one agent that inhibits KRAS G12C is MRTX849, or a pharmaceutically acceptable salt thereof.

134. The synergistic composition of any one of clauses 124 to 133, wherein the compound that inhibits FAK, SRC and JAK2 is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

135. The synergistic composition of any one of clauses 124 to 133, wherein the compound that inhibits FAK, SRC and JAK2 is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

136. The synergistic composition of any one of clauses 124 to 135, wherein the human body has not received a prior treatment.

137. The synergistic composition of any one of clauses 124 to 135, wherein the human body has received at least one prior treatment of one or more chemotherapeutic agents or immunotherapies.

138. The synergistic composition of any one of clauses 124 to 135 or 137, wherein the host animal is a human patient in need of such treatment who has received at least one prior treatment of one or more chemotherapeutic agents or immunotherapies, and/or developed an acquired resistance to the treatment, or developed bypass resistance to the treatment, and/or developed bypass resistance to the treatment regulated by FAK, SRC or JAK2.

BRIEF DESCRIPTION OF THE DRAWINGS

FIG. 2a is a chart showing the 2D dose response matrix after treatment of H2122 cells with a compound 1 and KRAS inhibitor AMG-510 at various concentrations from 0 nM to 3000 nM of Compound 1, and from 0 nM to 10000 nM KRAS inhibitor AMG-510.

FIG. 3g is a graph showing the effect of Compound 1 alone, MRTX849 alone, and the combination of Compound 1 and MRTX849 on IL6 mRNA expression from H2122 cells 24 and 48 hrs after treatment.

DETAILED DESCRIPTION

Figure 1A:
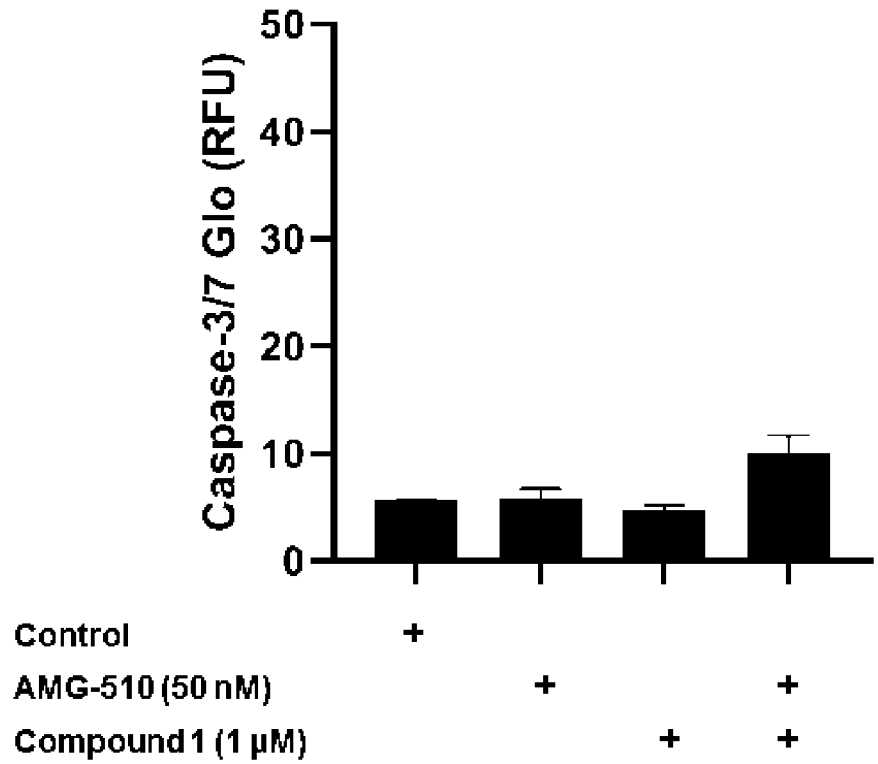
FIG. 1a shows the level of caspase-3/7 activated by Compound 1 (1 μM), AMG-510 (50 nM) and Compound 1 (1 μM)+AMG510 (50 nM) in H358 cells with KRAS G12C mutation after 24 hrs.
Figure 1B:
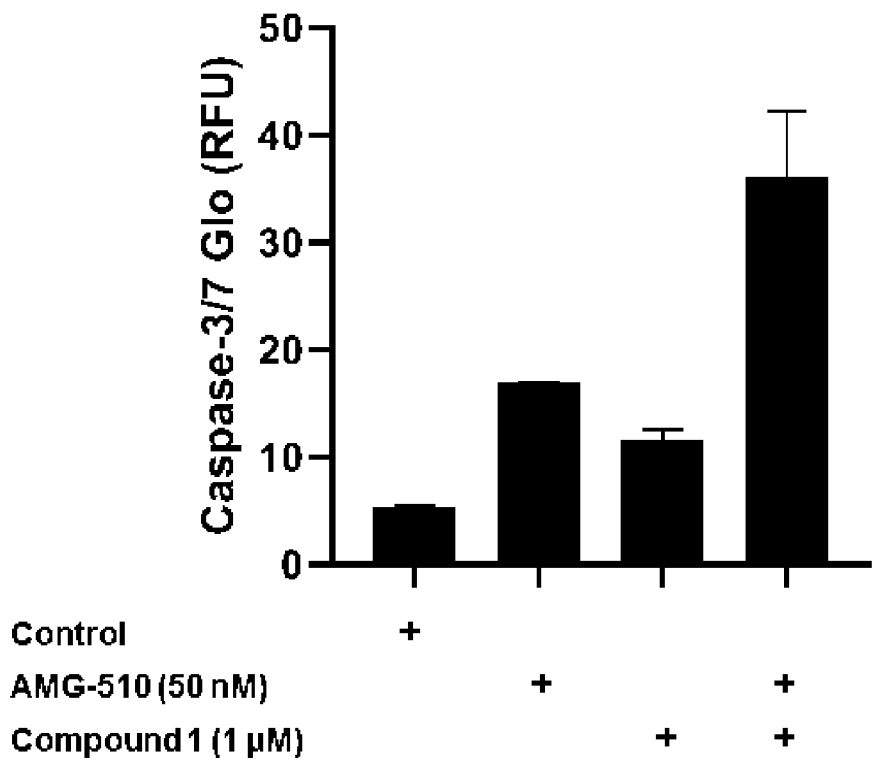
FIG. 1b shows the level of caspase-3/7 activated by Compound 1 (1 μM), AMG-510 (50 nM) and Compound 1 (1 μM)+AMG510 (50 nM) in H358 cells with KRAS G12C mutation after 48 hrs.
Figure 1C:
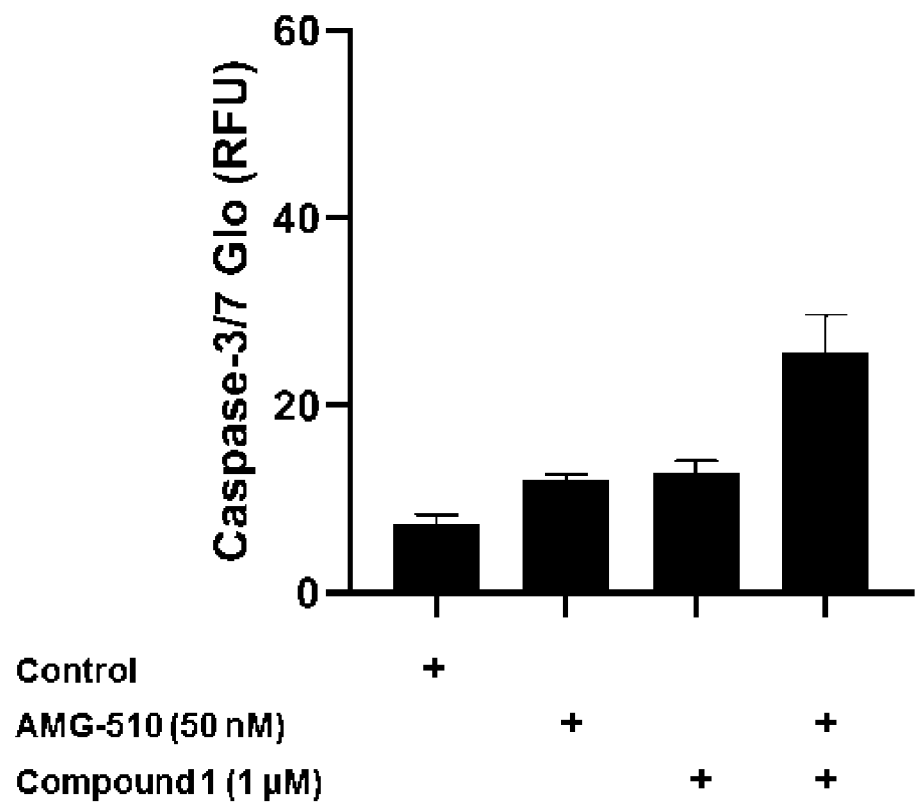
FIG. 1c shows the level of caspase-3/7 activated by Compound 1 (1 μM), AMG-510 (50 nM) and Compound 1 (1 μM)+AMG510 (50 nM) in H2122 cells with KRAS G12C mutation after 24 hrs.
Figure 1D:
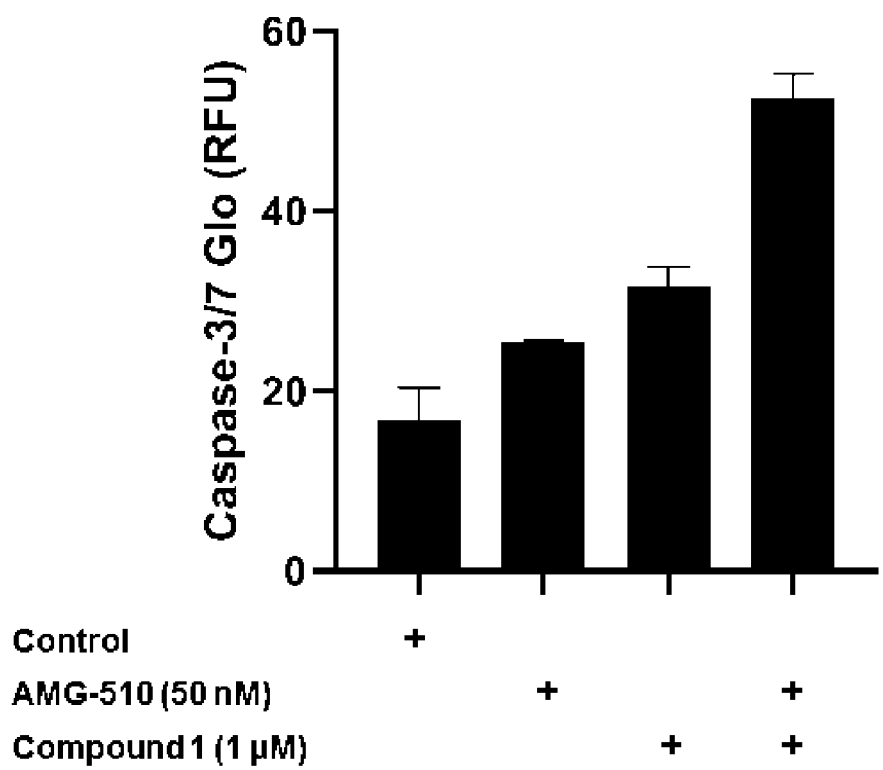
FIG. 1d shows the level of caspase-3/7 activated by Compound 1 (1 μM), AMG-510 (50 nM) and Compound 1 (1 μM)+AMG510 (50 nM) in H2122 cells with KRAS G12C mutation after 48 hrs.
Figure 1E:
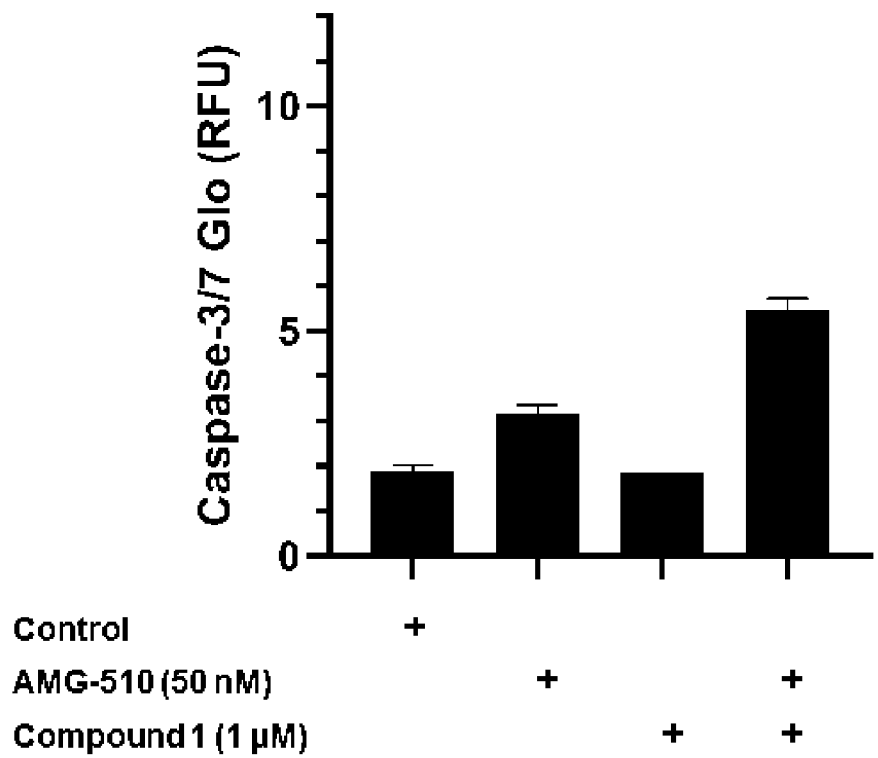
FIG. 1e shows the level of caspase-3/7 activated by Compound 1 (1 μM), AMG-510 (50 nM) and Compound 1 (1 μM)+AMG510 (50 nM) in H1373 cells with KRAS G12C mutation after 24 hrs.
Figure 1F:
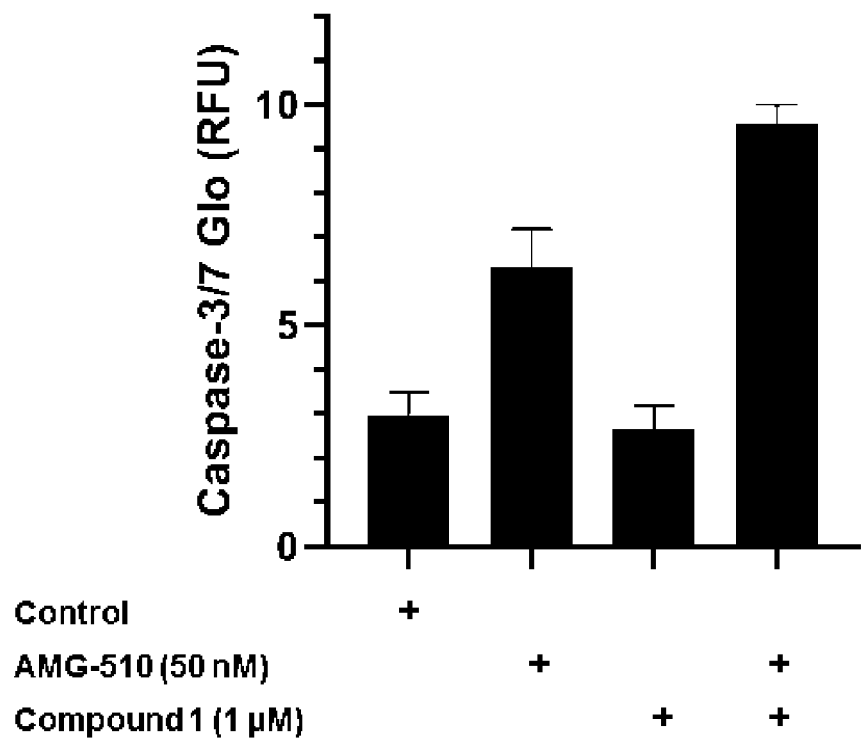
FIG. 1f shows the level of caspase-3/7 activated by Compound 1 (1 μM), AMG-510 (50 nM) and Compound 1 (1 μM)+AMG510 (50 nM) in H1373 cells with KRAS G12C mutation after 48 hrs.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such subcombination of chemical groups was individually and explicitly disclosed herein.

The methods described herein are used to treat a "host animal" with cancer in need of such treatment. In one embodiment, the methods described herein can be used for both human clinical medicine and veterinary applications. Thus, a "host animal" can be administered the combinations described herein, and the host animal can be human (e.g., a human patient, a.k.a. a patient) or, in the case of veterinary applications, can be a laboratory, agricultural, or domestic animal. In one aspect, the host animal can be a human, or a laboratory animal such as a rodent (e.g., mice, rats, etc.), and the like.

As used herein, the term "disease" includes, but is not limited to, cancer, pain, inflammatory diseases, such as allergy, asthma, autoimmune diseases, coeliac disease, glomerulonephritis, hepatitis, inflammatory bowel disease (e.g. ulcerative colitis), pre-perfusion injury, transplant rejection, psoriasis, and rheumatoid arthritis; polycythemia vera, essential thrombocythemia, and myeloid metaplasia with myelofibrosis.

As used herein, the term "cancer" includes, but is not limited to, ALCL, lung cancer, such as non-small cell lung cancer (NSCLC), including adenocarcinoma, lung squamous cell carcinoma, large cell carcinoma, and large cell neuroendocrine tumors, small cell lung cancer (SCLC), neuroblastoma, inflammatory myofibroblastic tumor, adult renal cell carcinoma, pediatric renal cell carcinoma, breast cancer, such as luminal A, luminal B, triple negative breast cancer, triple positive breast cancer, HER2+, and the like, colonic adenocarcinoma, glioblastoma, glioblastoma multiforme, thyroid cancer, such as anaplastic thyroid cancer, cholangiocarcinoma, ovarian cancer, gastric cancer, such as gastric adenocarcinoma, colorectal cancer (CRC), inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cancer, such as skin cutaneous melanoma, head and neck squamous cell carcinoma (HNSCC), pediatric glioma CML, prostate cancer, ovarian serous cystadenocarcinoma, skin cutaneous melanoma, castrate-resistant prostate cancer, Hodgkin lymphoma, uterine cancer, such as serous and clear cell endometrial cancer, endometrial cancer, and the like, oral cancer, endocrine cancer, esophageal cancer, laryngeal cancer, pancreatic cancer, colon cancer, bladder cancer, bone cancer, cervical cancer, testicular cancer, rectal cancer, kidney cancer, liver cancer, and stomach cancer. It will be appreciated that the term "cancer" includes both primary cancers or primary tumors and metastatic cancers or metastatic tumors, and includes all stages of cancer as known in the art. For example, metastatic NSCLC, metastatic CRC, metastatic pancreatic cancer, metastatic colorectal carcinoma, metastatic HNSCC, metastatic uterine cancer, and the like. It will be appreciated that the term "cancer" includes cancers that involve the upregulation of certain genes or genetic mutations in certain genes that can lead to disease progression, such as small GTPases (e.g. KRAS and the like) and receptor tyrosine kinases such as EGFR, and the like.

As used herein, the term "agent that inhibits KRAS G12C" includes, but is not limited to, any compound or agent known in the art to selectively inhibit the KRAS G12C gene or selectively inhibit the protein encoded by the KRAS G12C gene, referred to herein as K-Ras G12C, that is involved in the RAS/MAPK signaling pathway, where the K-Ras protein product of the KRAS gene has the missense mutation G12C. The terms KRAS gene, K-Ras, and RAS/MAPK signaling pathway will be known and understood by one of skill in the art. It will be appreciated that the KRAS G12C mutation encodes a glycine to cysteine mutation at position 12 of the K-Ras protein (a.k.a. K-Ras G12C). It will further be appreciated that the production of a K-Ras G12C protein as a gene product of the KRAS G12C gene can be the result of a coding sequence mutation, e.g. guanine to thymine substitution, at position 34 of the coding sequence. It will be further appreciated that the agent that inhibits KRAS G12C can be any agent known in the art that selectively targets the KRAS G12C gene, and includes those agents, such as siRNA, oligonucleotides, ribonucleic acids, and the like, that selectively inhibit or are capable of otherwise selectively interfering with the transcription (and/or translation) of the KRAS G12C gene (or its corresponding messenger RNA) to the K-Ras G12C protein. It will further be appreciated that an agent that inhibits KRAS G12C can be an agent capable of selectively inhibiting or otherwise selectively interfering with KRAS G12C transcription and/or translation of the corresponding messenger RNA can be a biological agent, such as a siRNA, oligonucleotide, ribonucleic acid, and the like. Alternatively, it will be appreciated that an agent that inhibits KRAS G12C can be an agent that selectively inhibits the protein encoded by the KRAS G12C gene having a coding sequence that produces a K-Ras G12C protein (e.g. a guanine to thymine substitution, at position 34 of the KRAS coding sequence) can be a biological agent, such as an antibody (e.g. a monoclonal antibody or mAh), a small molecule drug/inhibitor (e.g. small molecule inhibitor of KRAS G12C), or a targeted agent. Examples of "an agent that inhibits KRAS G12C" can include, but are not limited to AMG-510, MRTX849, JNJ-74699157 (a.k.a. ARS-3248), ARS-1620, MRTX1257, RM-007 or ADT-007. In some embodiments, the agent that inhibits KRAS G12C is a compound described in United States Patent Publication US20180334454, incorporated herein by reference for exemplary agents that inhibit KRAS G12C (a.k.a. exemplary small molecule inhibitor of KRAS G12C) and their preparation. In some embodiments, the agent that inhibits KRAS G12C is AMG510 having the formula

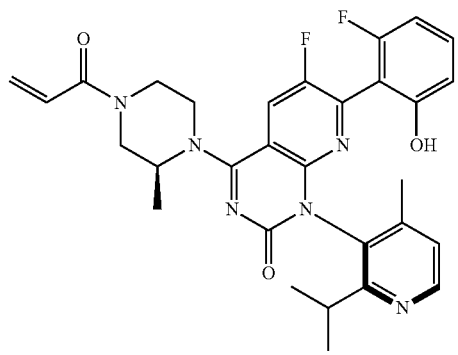

or a pharmaceutically acceptable salt thereof.

In some embodiments, the agent that inhibits KRAS G12C is a compound described in United States Patent Publications US20190270743 and US20190144444, incorporated herein by reference for exemplary agents that inhibit KRAS G12C (a.k.a. exemplary small molecule inhibitor of KRAS G12C) and their preparation. In some embodiments, the agent that inhibits KRAS G12C is MRTX849 having the formula

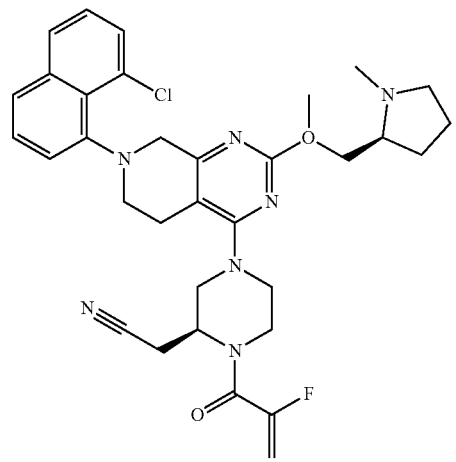

or a pharmaceutically acceptable salt thereof.

In some embodiments, the agent that inhibits KRAS G12C is AMG-510, MRTX849, or ARS-1620, or a pharmaceutically acceptable salt thereof.

Chemical Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbomenyl, 9H-fluoren-9-yl, and the like. Illustrative examples of cycloalkyl groups shown in graphical representations include the following entities, in the form of properly bonded moieties:

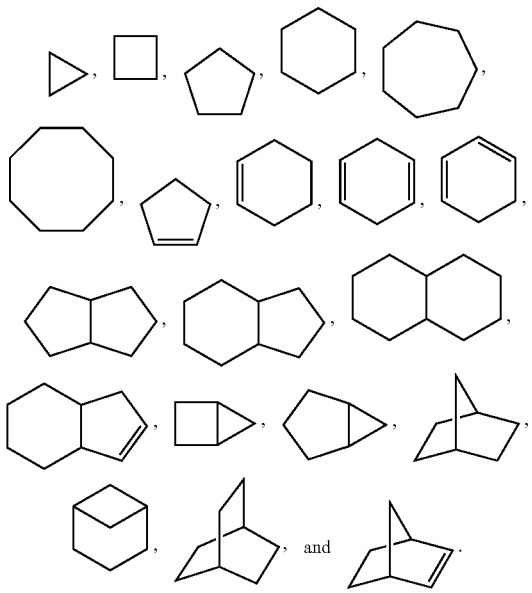

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

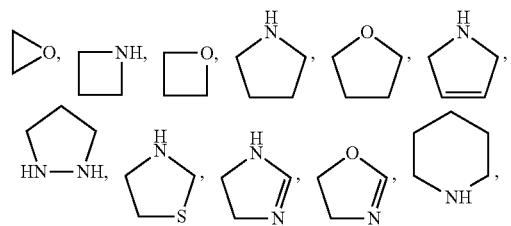

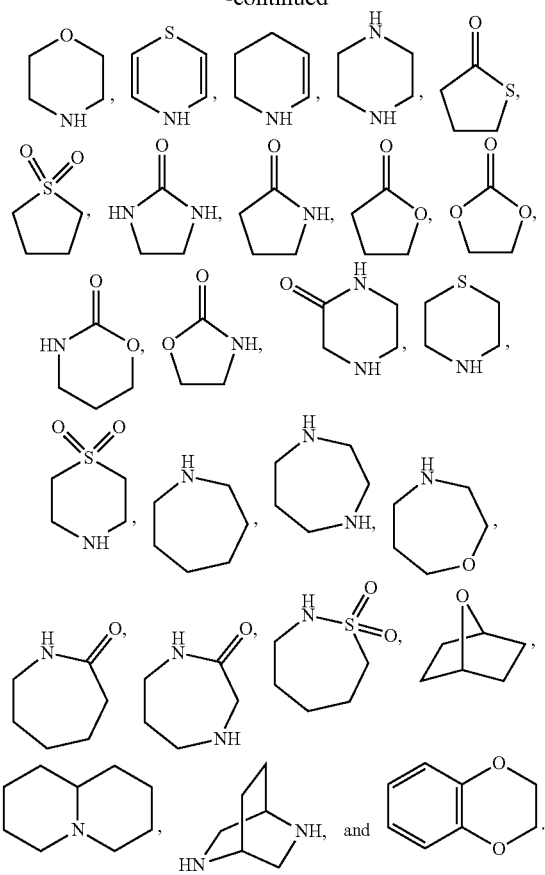

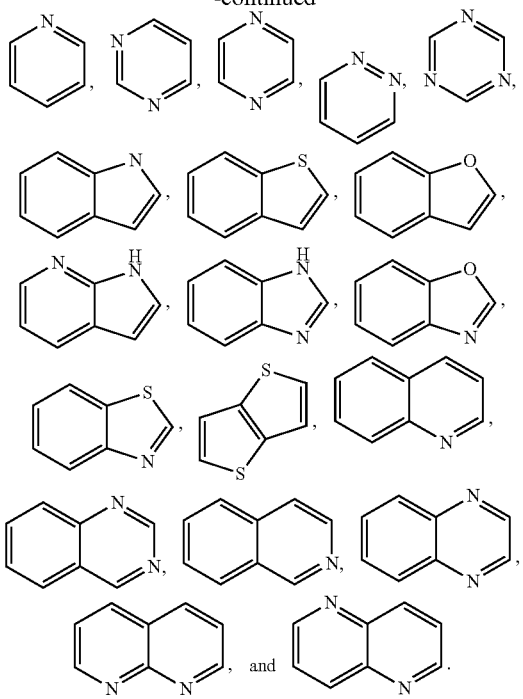

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

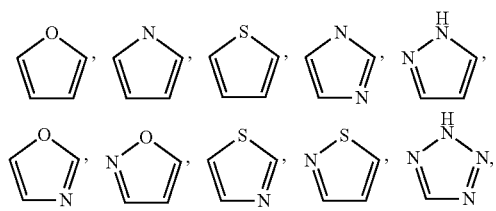

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents.

Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmacologically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bi sulfates, sulfites, bi sulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propyl sulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol " "$\sim\!\sim\!\sim$" " include both stereoisomers for the carbon atom to which the symbol " "$\sim\!\sim\!\sim$" " is attached, specifically both the bonds " "——▬" " and " "⬝⬝⬝⬝⬝" " are encompassed by the meaning of " "$\sim\!\sim\!\sim$" ". For example, in some exemplary embodiments, certain compounds provided herein can be described by the formula

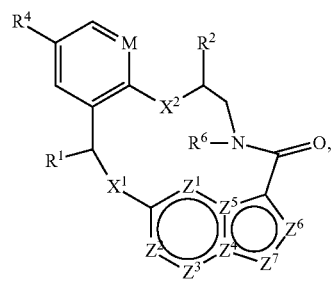

which formula will be understood to encompass compounds having all stereochemical configurations at the relevant carbon atoms, including

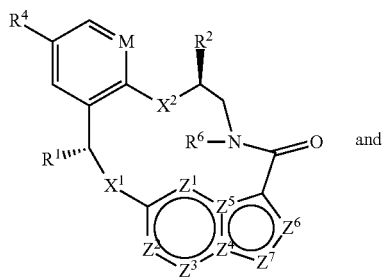

and

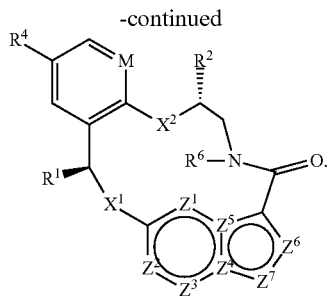

Embodiments

In some embodiments, the methods described herein relate to the treatment of cancer comprising administering to a patient in need of treatment a therapeutically effective amount of one or more compounds that inhibit FAK, SRC and/or JAK2 in combination with an agent that inhibits KRAS G12C. In some embodiments, the methods described herein relate to the treatment of cancer comprising administering to a patient in need of treatment a therapeutically effective amount of a compound that inhibits FAK, SRC and JAK2 in combination with an agent that inhibits KRAS G12C. It will be appreciated that an inhibitor is any substance that reduces or suppresses the activity of another substance, such as a cell surface receptor (i.e. a receptor tyrosine kinase), or a kinase (i.e. a non-receptor tyrosine kinase), or the transcription and/or translation of a gene. It will be appreciated that "a compound that inhibits FAK, SRC and JAK2" is a compound that has affinity for all three of the biological targets FAK, SRC and JAK2.

It has been discovered that certain compounds described herein have been surprisingly shown to be inhibitors of FAK, SRC and JAK2, and can be used in combination with an agent that inhibits KRAS G12C to treat cancer in a patient in need of such treatment. In some embodiments, the combination of one or more compounds that inhibit FAK, SRC and/or JAK2 with an agent that inhibits KRAS G12C can provide a synergistic response in a patient in need of treatment for cancer. In some embodiments, the combination of a compound that inhibits FAK, SRC and JAK2 with an agent that inhibits KRAS G12C can provide a synergistic response in a patient in need of treatment for cancer. In some embodiments, methods for treating cancer comprising administering a combination of a therapeutically effective amount of a compound that inhibits FAK, SRC and JAK2 and a therapeutically effective amount of an agent that inhibits KRAS G12C. In some embodiments, the compound that inhibits FAK, SRC and JAK2 and the agent that inhibits KRAS G12C are co-formulated. In some embodiments, the compound that inhibits FAK, SRC and JAK2 and the agent that inhibits KRAS G12C are administered at the same time. In some embodiments, the compound that inhibits FAK, SRC and JAK2 and the agent that inhibits KRAS G12C are individually formulated, and administered at the same time. In some embodiments, the compound that inhibits FAK, SRC and JAK2 and the agent that inhibits KRAS G12C are individually formulated, and administered in sequence. In some embodiments, the sequential administration of the compound that inhibits FAK, SRC and JAK2 and the agent that inhibits KRAS G12C can be accomplished with the compound that inhibits FAK, SRC and JAK2 administered first, and the agent that inhibits KRAS G12C administered second. In some embodiments, the sequential administration of the compound that inhibits FAK, SRC and JAK2 and the agent that inhibits KRAS G12C can be accomplished with the agent that inhibits KRAS G12C administered first, and the compound that inhibits FAK, SRC and JAK2 administered second.

In some embodiments, the compound that inhibits FAK, SRC and JAK2 is of the formula I

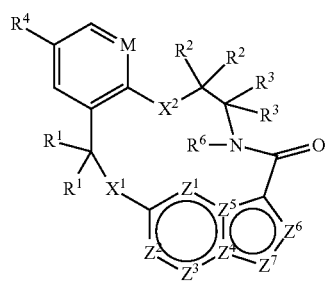

I wherein
M is $CR^5$ or N;
$X^1$ and $X^2$ are independently $-C(R^7)(R^8)-$, $-S-$, $-S(O)-$, $-S(O)_2-$, $-O-$ or $-N(R^9)-$;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, $-C(O)OR^7$ or $-C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, $-OH$, $-CN$, $-OC_1$-$C_6$ alkyl, $-NH_2$, $-NH(C_1$-$C_6$ alkyl), $-N(C_1$-$C_6$ alkyl)$_2$, $-NHC(O)C_1$-$C_6$ alkyl, $-N(C_1$-$C_6$ alkyl)C(O)C_1$-$C_6$ alkyl, $-NHC(O)NH_2$, $-NHC(O)NHC_1$-$C_6$ alkyl, $-N(C_1$-$C_6$ alkyl)C(O)NH_2$, $-N(C_1$-$C_6$ alkyl)C(O)NHC_1$-$C_6$ alkyl, $-NHC(O)N(C_1$-$C_6$ alkyl)$_2$, $-N(C_1$-$C_6$ alkyl)C(O)N(C_1$-$C_6$ alkyl)$_2$, $-NHC(O)OC_1$-$C_6$ alkyl, $-N(C_1$-$C_6$ alkyl)C(O)OC_1$-$C_6$ alkyl, $-NHS(O)(C_1$-$C_6$ alkyl), $-NHS(O)_2(C_1$-$C_6$ alkyl), $-N(C_1$-$C_6$ alkyl)S(O)(C_1$-$C_6$ alkyl), $-N(C_1$-$C_6$ alkyl)S(O)_2(C_1$-$C_6$ alkyl), $-NHS(O)NH_2$, $NHS(O)_2NH_2$, $-N(C_1$-$C_6$ alkyl)S(O)NH_2$, $-N(C_1$-$C_6$ alkyl)S(O)_2NH_2$, $-NHS(O)NH(C_1$-$C_6$ alkyl), $-NHS(O)_2NH(C_1$-$C_6$ alkyl), $-NHS(O)N(C_1$-$C_6$ alkyl)$_2$, $-NHS(O)_2N(C_1$-$C_6$ alkyl)$_2$, $-N(C_1$-$C_6$ alkyl)S(O)NH(C_1$-$C_6$ alkyl), $-N(C_1$-$C_6$ alkyl)S(O)_2NH(C_1$-$C_6$ alkyl), $-N(C_1$-$C_6$ alkyl)S(O)N(C_1$-$C_6$ alkyl)$_2$, $-N(C_1$-$C_6$ alkyl)S(O)_2N(C_1$-$C_6$ alkyl)$_2$, $-CO_2H$, $-C(O)C_1$-$C_6$ alkyl, $-C(O)NH_2$, $-C(O)NH(C_1$-$C_6$ alkyl), $-C(O)N(C_1$-$C_6$ alkyl)$_2$, $-SC_1$-$C_6$ alkyl, $-S(O)C_1$-$C_6$ alkyl, $-S(O)_2C_1$-$C_6$ alkyl, $-S(O)NH(C_1$-$C_6$ alkyl), $-S(O)_2NH(C_1$-$C_6$ alkyl), $-S(O)N(C_1$-$C_6$ alkyl)$_2$, $-S(O)_2N(C_1$-$C_6$ alkyl)$_2$, $-P(C_1$-$C_6$ alkyl)$_2$, $-P(O)(C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, $-C(O)OR^7$ or $-C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, $-OH$, $-CN$, $-OC_1$-$C_6$ alkyl, $-NH_2$, $-NH(C_1$-$C_6$ alkyl), $-N(C_1$-$C_6$ alkyl)$_2$, $NHC(O)C_1$-$C_6$ alkyl, $-N(C_1$-$C_6$ alkyl)C(O)C_1$-$C_6$ alkyl, $-NHC(O)NH_2$, $-NHC(O)NHC_1$-$C_6$ alkyl, $-N(C_1$-$C_6$ alkyl)C(O)NH_2$, $-N(C_1$-$C_6$ alkyl)C(O)NHC_1$-$C_6$ alkyl, $-NHC(O)N(C_1$-$C_6$ alkyl)$_2$, $-N(C_1$-$C_6$ alkyl)C(O)N(C_1$-$C_6$ alkyl)$_2$, $-NHC(O)OC_1$-$C_6$ alkyl, $-N(C_1$-$C_6$ alkyl)C(O)OC_1$-$C_6$ alkyl, $-NHS(O)(C_1$-$C_6$ alkyl), $-NHS(O)_2(C_1$-$C_6$ alkyl), $-N(C_1$-$C_6$ alkyl)S(O)(C_1$-$C_6$ alkyl), $-N(C_1$-$C_6$ alkyl)S(O)_2(C_1$-$C_6$ alkyl), $-NHS(O)NH_2$, $NHS(O)_2NH_2$, $-N(C_1$-$C_6$ alkyl)S(O)NH_2$, $-N(C_1$-$C_6$ alkyl)S(O)_2NH_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

In some embodiments, R$^1$ is H or C$_1$-C$_6$ alkyl. In some embodiments, R$^1$ is H or methyl. In some embodiments, one of R$^1$ is H and the other of R$^1$ is methyl. In some embodiments, R$^2$ is H. In some embodiments, R$^2$ is C$_1$-C$_6$ alkyl. In some embodiments, one of R$^2$ is H and the other of R$^2$ is methyl. In some embodiments, X$^1$ is —NR$^9$—. In some embodiments, R$^9$ is H. In some embodiments, X$^1$ is CHR$^7$. In some embodiments, R$^7$ is H. In some embodiments, X$^2$ is —O—. In some embodiments, R$^6$ is H. In some embodiments, R$^4$ is F. In some embodiments, M is CR$^5$, and R$^5$ is H.

Macrocyclic compounds that have been shown herein to be potent small-molecule multi-target kinase inhibitors showing activity against FAR, SRC and JAK2 include, but are not limited to, (7S,13R)-11-fluoro-7,13-dimethyl-6,7,13, 14-tetrahydro-1,15-ethenopyrazolo[4,3-f][1,4,8,10]benzoxatriazacyclotridecin-4(5H)-one (also herein referred to as "Compound 1"), represented by the formula

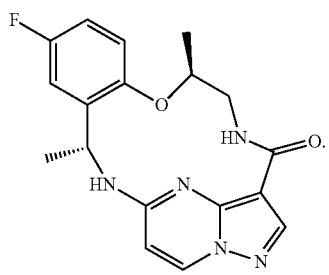 [SMILES: C[C@H]1CNC(=O)c2cnn3ccc(nc23)N[C@H](C)c2cc(F)ccc2O1]

Compound 1 has properties, including anti-tumor properties, which are pharmacologically mediated through inhibition of receptor and non-receptor tyrosine kinases. Compound 1 is disclosed in International Patent Publication WO2015/112806, which is incorporated herein by reference for the preparation of Compound 1.

In some embodiments of the above aspects, the compound that inhibits FAK, SRC and JAK2 is of the formula

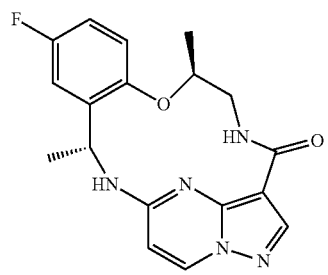 [SMILES: C[C@H]1CNC(=O)c2cnn3ccc(nc23)N[C@H](C)c2cc(F)ccc2O1]

or a pharmaceutically acceptable salt thereof.

It will be appreciated that the cancer can be any cancer that may be mediated by or associated with KRAS G12C, or the upregulation of KRAS G12C, including but not limited to, ALCL, NSCLC, neuroblastoma, inflammatory myofibroblastic tumor, adult renal cell carcinoma, pediatric renal cell carcinoma, breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer, stomach cancer and lung cancer.

In some embodiments, the present disclosure provides methods of treating disease in a patient that has received no prior treatment. In some embodiments, the present disclosure provides methods of treating disease in a patient that has received a prior treatment with one or more therapeutic agents. In some embodiments, the patient has been previously treated with one or more chemotherapeutic agents. In still other embodiments, the patent has been previously treated with one or more chemotherapeutic agents or immunotherapies and developed an acquired resistance to the treatment. In still other embodiments, the patent has been previously treated with one or more chemotherapeutic agents or immunotherapies and developed bypass resistance to the treatment. In still other embodiments, the patent has been previously treated with one or more chemotherapeutic agents or immunotherapies and developed bypass resistance to the treatment regulated by FAK, SRC or JAK2, and/or FAK.

Other chemotherapeutic agents which the patient may be been treated with prior to treatment with one or more of the compounds or biological agents described herein include but are not limited to kinase inhibitors, adrenocorticoids and corticosteroids, alkylating agents, peptide and peptidomimetic signal transduction inhibitors, antiandrogens, antiestrogens, androgens, aclamycin and aclamycin derivatives, estrogens, antimetabolites, platinum compounds, amanitins, plant alkaloids, mitomycins, discodermolides, microtubule inhibitors, epothilones, inflammatory and proinflammatory agents, purine analogs, pyrimidine analogs, camptothecins, dolastatins, and or immunotherapies. In some embodiments, the patient has been administered a prior treatment for NSCLC, such as pembrolizumab, platinum, platinum doublet, pemetrexed, carboplatin, paclitaxel, bevacizumab, atezolizumab, abraxane, and combinations thereof. In some embodiments, the patient has been administered a prior treatment for NSCLC cancer that is the standard of care using one or more agents selected from the group consisting of pembrolizumab, platinum, platinum doublet, pemetrexed, carboplatin, paclitaxel, bevacizumab, atezolizumab, and abraxane.

In some embodiments, the patient has been administered a prior treatment for colorectal cancer, such as fluorouracil (5-FU), leucovorin, irinotecan, oxaliplatin, capecitabine, bevacizumab, cetuximab, panitumumab, ziv-aflibercept, ramucirumab, pemborlizumab, nivolumab, ipilimumab, encorafenib, binimetinib, and combinations thereof. In some embodiments, the patient has been administered a prior treatment for colorectal cancer that is the standard of care using one or more agents selected from the group consisting of FOLFOX (i.e. 5-FU+leucovorin+irinotecan)+/−bevacizumab, panitumumab or cetuximab, CAPEOX (i.e. oxaliplatin+capecitabine)+/−bevacizumab, FOLFIRI (i.e. 5-FU+leucovorin+irinotecan)+/−bevacizumab, cetuximab, panitumumab, ziv-aflibercept or ramucirumab, FOLFOXIRI (i.e. irinotecan, oxaliplatin, leucovorin, 5-FU), irinotecan+cetuximab, panitumumab, or amucirumab, pemborlizumab, nivolumab, nivolumab+ipilimumab, encorafenib, and binimetinib.

In some embodiments, the patient has been administered a prior treatment for pancreatic cancer, such as fluorouracil (5-FU), leucovorin, irinotecan, liposomal irinotecan, oxaliplatin, gemcitabine, abraxane, erlotinib, capecitabine, and combinations thereof. In some embodiments, the patient has been administered a prior treatment for pancreatic cancer that is the standard of care using one or more agents selected from the group consisting of FOLFIRINOX (i.e. 5-FU+leucovorin+irinotecan+oxaliplatin), gemcitabine+abraxane, gemcitabine+erlotinib, gemcitabine, 5-FU+liposomal irinotecan, FOLFIRI (i.e. 5-FU+leucovorin+irinotecan), FOLFOX (i.e. 5-FU, oxaliplatin, leucovorin), and capecitabine+/−oxaliplatin.

In some embodiments, the patient has been administered a prior treatment for uterine cancer (a.k.a. endometrial cancer), such as carboplatin, cisplatin, paclitaxel, docetaxel, doxorubicin, liposomal doxorubicin, trastuzumab, topotecan, bevacizumab, temsirolimus tamoxifen, fulvestrant, an aromatase inhibitor, and combinations thereof. In some embodiments, the patient has been administered a prior treatment for pancreatic cancer that is the standard of care using one or more agents selected from the group consisting of carboplatin+paclitaxel+/−trastuzumab, carboplatin or cisplatin+docetaxel, doxorubicin, or paclitaxel, liposomal doxorubicin, topotecan, bevacizumab, temsirolimus tamoxifen, fulvestrant, and an aromatase inhibitor.

It will be appreciated that the agent that inhibits KRAS G12C for use in connection with the combination therapy described herein can be any agent that inhibits KRAS G12C as defined herein. Suitable examples of agent that inhibits KRAS G12C include antibodies of KRAS G12C, siRNAs, ribonucleic acids, peptides, oligonucleotides, small molecule inhibitors of KRAS G12C (as described herein), and the like. In some embodiments, the agent that inhibits KRAS G12C can be AMG-510, MRTX849, JNJ-74699157 (a.k.a. ARS-3248), ARS-1620, MRTX1257, RM-007 or ADT-007.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 2 g daily, or about 1 mg to 50 mg daily, or about 50 to 250 mg daily, or about 250 mg to 1 g daily. An alternative exemplary dose is in the range of about from about 0.1 mg/kg to 1 g/kg, or about 0.1 mg/kg to 5 mg/kg, or about 0.1 mg/kg to 1 mg/kg, or about 0.1 mg/kg to 0.6 mg/kg. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to affect transdermal delivery.

Dosing and Administration

In some embodiments of the methods and compositions described herein, a therapeutically effective amount of one or more compounds that inhibits FAK, SRC, and/or JAK2 in combination with a therapeutically effective amount of at least one agent that inhibits KRAS G12C is administered to a host animal, such as a human patient, in need of treatment for cancer. In some embodiments of the methods and compositions described herein, a therapeutically effective amount of a compound that inhibits FAK, SRC, and JAK2, in particular Compound 1, in combination with a therapeutically effective amount of at least one agent that inhibits KRAS G12C is administered to a host animal, such as a human patient, in need of treatment for cancer.

As used herein, the term "in combination with" refers to the administration of one or more compounds that inhibits FAK, SRC, and/or JAK2, in particular Compound 1, with at least one agent that inhibits KRAS G12C. It will be appreciated that the administration of one or more compounds that inhibits FAK, SRC, and/or JAK2, in particular Compound 1, "in combination with" administration of at least one agent that inhibits KRAS G12C at the same time as on another, where one or more compounds that inhibits FAK, SRC, and/or JAK2, in particular Compound 1 is administered before at least one agent that inhibits KRAS G12C, or where one or more compounds that inhibits FAK, SRC, and/or JAK2, in particular Compound 1 is administered after at least one agent that inhibits KRAS G12C. Furthermore, where the administration of one or more compounds that inhibits FAK, SRC, and/or JAK2, in particular Compound 1, occurs at the same time as administration of at least one agent that inhibits KRAS G12C, the administered compounds can be co-formulated in a composition or medicament, or can be administered at the same time as separate compositions or medicaments.

As used herein, the term "therapeutically effective amount" refers to that amount of active compound or pharmaceutical agent that elicits the biological or medicinal response in a patient, which includes alleviation of the symptoms of the disease or disorder being treated. In one aspect, the therapeutically effective amount is that which may treat or alleviate the disease or symptoms. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors.

In some embodiments, a therapeutically effective amount of the combination can be a synergistic combination that provides an enhanced response to treatment with the combination when compared to when the one or more compounds that inhibits FAK, SRC, and/or JAK2 and the at least one agent that inhibits KRAS G12C are administered individually. In some embodiments, the synergistic effect provided by the administration of a therapeutically effective amount of the combination of the one or more compounds that inhibits FAK, SRC, and/or JAK2 and the at least one agent that inhibits KRAS G12C is a dose response that is more than additive compared to the response of the each of the components of the combination administered individually.

In some embodiments, a therapeutically effective amount of the combination can be a synergistic combination that provides an enhanced response to treatment with the combination when compared to when the compound that inhibits FAK, SRC, and JAK2, in particular Compound 1, and the at least one agent that inhibits KRAS G12C are administered individually. In some embodiments, the synergistic effect provided by the administration of a therapeutically effective amount of the combination of the compound that inhibits FAK, SRC, and JAK2, in particular Compound 1, and the at least one agent that inhibits KRAS G12C is a dose response that is more than additive compared to the response of the each of the components of the combination administered individually.

In some embodiments, an exemplary dose for each compound or agent individually in the various methods and compositions described herein is in the range of about from about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g. It will be appreciated that all possible subranges within the dose ranges described above are contemplated and described herein. For example, a dose range of about 150 to about 500 mg for a compound that inhibits FAK, SRC, and JAK2, in particular Compound 1, provided in the methods and compositions described herein includes doses of about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, including all possible doses and ranges as may be required based on such factors for determining a therapeutically effective amount as described herein. In some embodiments, the compound that inhibits FAK, SRC, and JAK2, in particular Compound 1, provided in the methods and compositions described herein can be dosed at about 40 mg, about 80 mg, about 120 mg, or about 160 mg.

In some embodiments, an exemplary dose for each compound or agent individually in the various methods and compositions described herein is in the range of about from about 0.1 mg to about 3 g daily, or about 1 mg to about 50 mg daily, or about 50 to about 250 mg daily, or about 150 to about 500 mg daily, or about 150 to about 250 mg daily, or about 250 mg to about 1 g daily, or about 100 mg to about 2 g daily, or about 500 mg to about 2 g daily, or about 500 mg to about 1 g daily. It will be appreciated that all possible subranges within the daily dose ranges described above are contemplated and described herein. For example, a dose range of about 150 to about 500 mg daily for a compound that inhibits FAK, SRC, and JAK2, in particular Compound 1, provided in the methods and compositions described herein includes doses of about 150 mg daily, about 160 mg daily, about 170 mg daily, about 180 mg daily, about 190 mg daily, about 200 mg daily, about 210 mg daily, about 220 mg daily, about 230 mg daily, about 240 mg daily, and about 250 mg daily, about 260 mg daily, about 270 mg daily, about 280 mg daily, about 290 mg daily, about 300 mg daily, about 310 mg daily, about 320 mg daily, about 330 mg daily, about 340 mg daily, about 350 mg daily, about 360 mg daily, about 370 mg daily, about 380 mg daily, about 390 mg daily, about 400 mg daily, about 410 mg daily, about 420 mg daily, about 430 mg daily, about 440 mg daily, about 450 mg daily, about 460 mg daily, about 470 mg daily, about 480 mg daily, about 490 mg daily, about 500 mg daily, including all possible doses and ranges as may be required based on such factors for determining a therapeutically effective amount as described herein. In some embodiments, the compound that inhibits FAK, SRC, and JAK2, in particular Compound 1, provided in the methods and compositions described herein can be dosed at about 40 mg daily, about 80 mg daily, about 120 mg daily, or about 160 mg daily.

In some embodiments, an alternative exemplary dose for each compound or agent individually in the various methods and compositions described herein is in the range of about from about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg. It will be appreciated that all possible subranges within the dose ranges described above are contemplated and described herein. For example, a dose range of about 1.0 mg/kg to about 10 mg/kg for a compound that inhibits FAK, SRC, and JAK2, in particular Compound 1, provided in the methods and compositions described herein includes doses of about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, and about 10.0 mg/kg, including all possible doses and ranges as may be required based on such factors for determining a therapeutically effective amount as described herein.

In some embodiments, an alternative exemplary dose for each compound or agent individually in the various methods and compositions described herein is in the range of about from about 0.1 mg/kg to about 1 g/kg daily, or about 0.5 mg/kg to about 50 mg/kg daily, or about 0.5 mg/kg to about 25 mg/kg daily, or about 1.0 mg/kg to about 10 mg/kg daily, or about 1.0 mg/kg to about 5 mg/kg daily, or about 0.1 mg/kg to about 5 mg/kg daily, or about 0.1 mg/kg to about 1 mg/kg daily, or about 0.1 mg/kg to about 0.6 mg/kg daily. It will be appreciated that all possible subranges within the dose ranges described above are contemplated and described herein. For example, a dose range of about 1.0 mg/kg to about 10 mg/kg daily for a compound that inhibits FAK, SRC, and JAK2, in particular Compound 1, provided in the methods and compositions described herein includes doses of about 1.0 mg/kg daily, about 2.0 mg/kg daily, about 3.0 mg/kg daily, about 4.0 mg/kg daily, about 5.0 mg/kg daily, about 6.0 mg/kg daily, about 7.0 mg/kg daily, about 8.0 mg/kg daily, about 9.0 mg/kg daily, and about 10.0 mg/kg daily, including all possible doses and ranges as may be required based on such factors for determining a therapeutically effective amount as described herein.

It will be appreciated that various dosing schedules for administration of each compound or agent administered individually (or together) can be applied to the methods and compositions described herein. It will be further appreciated that a dosing schedule for each compound or agent administered individually (or together) in the various methods and compositions described herein can be defined by cycles of the dosing schedule, where such cycles are defined by the number of days of treatment, number of doses of each compound or agent individually (or together), the total dose of each compound or agent individually (or together), and the like. In some embodiments, a host animal, such as a human patient in need of treatment, can be administered each compound or agent administered individually (or together) for at least one cycle, for at least two cycles, for at least three cycles, for at least four cycles, and the like. Alternatively, in some embodiments, a host animal, such as a human patient in need of treatment, can be administered each compound or agent administered individually (or together) for from 1 to about 50 cycles, from 1 to about 25 cycles, from 1 to about 20 cycles, from 1 to about 10 cycles, and the like. It will be appreciate that, in some embodiments, a dosing schedule for each compound or agent administered individually (or together) in the various methods and compositions described herein can include a holiday period during which no compound or agent is administered, and such holiday period can be measured in days. In some embodiments, a dosing schedule for each compound or agent administered individually (or together) in the various methods and compositions described herein can be defined by a number of cycles as described herein, followed by a holiday period, followed by another number of cycles as described herein.

In some embodiments, an exemplary dosing schedule for each compound or agent individually in the various methods and compositions described herein can include administration of a single daily dose (QD) or divided dosage units (e.g., BID (twice daily), TID (three times daily), QID (four times daily)). In some embodiments, a dosing schedule for each compound or agent in the various methods and compositions described herein can be the same, such as all compounds or agents in the various methods and compositions described herein are administered QD, BID, or the like. In some embodiments, a dosing schedule for each compound or agent in the various methods and compositions described herein can be different from each other, such as one compound or agent in the various methods and compositions described herein is administered QD, and another compound or agent in the various methods and compositions described herein is administered BID. In some embodiments, a dosing schedule for each compound or agent in the various methods and compositions described herein can vary within a cycle, such as one compound or agent in the various methods and compositions described herein administered QD for a set number of days (e.g. QD for 1 day, 2 days, 3 days, 4 days, etc) followed by BID for a set number of days (e.g. BID for 1 day, 2 days, 3 days, 4 days, etc). In some embodiments, a dosing schedule for each compound or agent in the various methods and compositions described herein can be the same or different within a cycle, such as one compound or agent in the various methods and compositions described herein administered QD for a set number of days (e.g. QD for 1 day, 2 days, 3 days, 4 days, etc) followed by BID for a set number of days (e.g. BID for 1 day, 2 days, 3 days, 4 days, etc) to match the length of the cycle, and another compound or agent administered BID for a set number of days to match the length of the cycle.

In some embodiments, the compound that inhibits FAK, SRC, and JAK2, in particular Compound 1, and the agent that inhibits KRAS G12C are administered at the same time. In some embodiments, the compound that inhibits FAK, SRC, and JAK2, in particular Compound 1, and the agent that inhibits KRAS G12C are individually formulated, and administered at the same time. In some embodiments, the compound that inhibits FAK, SRC, and JAK2, in particular Compound 1, and the agent that inhibits KRAS G12C are individually formulated, and administered in sequence. In some embodiments, the sequential administration of the compound that inhibits FAK, SRC, and JAK2, in particular Compound 1, and the agent that inhibits KRAS G12C can be accomplished with the compound that inhibits FAK, SRC and JAK2, in particular Compound 1, administered first (e.g. in the morning), and the agent that inhibits KRAS G12C administered second (e.g. in the afternoon or evening). In some embodiments, the sequential administration of the compound that inhibits FAK, SRC, and JAK2, in particular Compound 1, and the agent that inhibits KRAS G12C can be accomplished with agent that inhibits KRAS G12C administered first (e.g. in the morning), and the compound that inhibits FAK, SRC, and JAK2, in particular Compound 1, administered second (e.g. in the afternoon or evening).

In some embodiments, an exemplary dosing schedule for each compound or agent individually in the various methods and compositions described herein can include administration of a compound that inhibits FAK, SRC, and JAK2, in particular Compound 1, at a dose level of from about 100 mg to about 300 mg QD for at least one day followed by a dose level of from about 100 mg to about 300 mg BID and an agent that inhibits KRAS G12C, in particular AMG510, at a dose level of from about 800 mg to about 1.5 g QD. In some embodiments, the administration of a compound that inhibits FAK, SRC, and JAK2, in particular Compound 1, and an agent that inhibits KRAS G12C, in particular AMG510, on the dose schedule described above can be given for from 1 to about 20 cycles, where each cycle is from about 5 to about 20 days. In some embodiments, the administration of a compound that inhibits FAK, SRC, and JAK2, in particular Compound 1, and an agent that inhibits KRAS G12C, in particular AMG510, on the dose schedule described above can be given for a set number of days, such as from about 20 to about 200 days, perpetually, or until treatment is stopped by a treating physician.

In some embodiments, an exemplary dosing schedule for each compound or agent individually in the various methods and compositions described herein can include administration of a compound that inhibits FAK, SRC, and JAK2, in particular Compound 1, at a dose level of from about 100 mg to about 300 mg QD for at least one day followed by a dose level of from about 100 mg to about 300 mg BID and an agent that inhibits KRAS G12C, in particular MRTX849, at a dose level of from about 500 mg to about 1 g BID. In some embodiments, the administration of a compound that inhibits FAK, SRC, and JAK2, in particular Compound 1, and an agent that inhibits KRAS G12C, in particular MRTX849, on the dose schedule described above can be given for from 1 to about 20 cycles, where each cycle is from about 5 to about 20 days. In some embodiments, the administration of a compound that inhibits FAK, SRC, and JAK2, in particular Compound 1, and an agent that inhibits KRAS G12C, in particular MRTX849, on the dose schedule described above can be given for a set number of days, such as from about 20 to about 200 days, perpetually, or until treatment is stopped by a treating physician.

EXAMPLES

Chemicals and Reagents

Compound 1 was prepared according to the methods described in WO2015/112806, see specifically Example 90 as described therein. WO2015/112806 is incorporated herein by reference for the preparation of Compound 1.

AMG510 was purchased from Active Biochem (catalog number A-9132). Drugs were prepared in dimethyl sulfoxide (DMSO) at a concentration of 10-100 mmol/L stock solutions and stored at −20° C. Further dilutions were made in culture medium to final concentration before use. Phospho-STAT3 (Tyr705), phospho-AKT (Ser473), phospho-ERK1/2 (Thr202/Tyr204), phospho-FAK (Tyr576/577), STAT3, FAK, SRC, ART, ERK, PARP, cleaved caspase-3, tubulin, and actin were purchased from Cell Signaling Technology (Beverly, Mass.).

Cell Lines

Human NSCLC cell lines H358, H23, H2122, H1373 and H1792, harboring KRAS G12C mutation, were purchased from the American Type Culture Collection (ATCC). All cell lines were maintained in RPMI (Roswell Park Memorial Institute medium) 1640 supplemented with 1% penicillin/streptomycin/glutamine (Gibco) and 10% fetal bovine serum (FBS) (Gibco) in 5% $CO_2$, 37° C. cell culture incubator and were routinely evaluated for *mycoplasma* contamination.

In-Vitro Assays

Example 1: Cell Viability Assay

Two thousand cells per well were seeded in 96 or 384 well white plate, and then treated with indicated compounds for 72 hours (37° C., 5% $CO_2$). Cell proliferation was measured using CellTiter-Glo luciferase-based ATP detection assay (Promega) following the manufactures's protocol. $IC_{50}$ determinations were performed using GraphPad Prism software (GraphPad, Inc., San Diego, Calif.).

Results showing cell viability % of the KRAS G12C inhibitor (AMG510), Compound 1, and the combination of the KRAS inhibitor AMG510 with Compound 1 (1 μM) in KRAS G12C mutated H358, H23, H2122, H1373 and H1792 cells are summarized in Table 1. Although H358, H23, H2122, H1373 and H1792 NSCLC cell line endogenously expresses KRAS G12C mutation, the KRAS G12C inhibitor AMG510 demonstrated moderate to weak inhibition of the cell proliferation. We investigated the synergistic effect of Compound 1 (1 μM) in combination with AMG510 on cell proliferation in H358, H23, H2122, H1373 and H1792 NSCLC cell lines with KRAS G12C mutation. Compound 1 alone had only weak inhibition activity to H358, H23, H2122, H1373 and H1792 NSCLC cell line with $IC_{50}$ ranges from 1.9 to 5 μM. A strong synergy was observed with the combination of AMG510 and Compound 1. Compound 1 at 1 μM concentration shifted AMG510's $IC_{50}$ from 213 nM to 3 nM against H358 cell proliferation. The combination caused much more complete cell proliferation suppression compared to AMG510 treatment alone in H23, H2122, H1372, and H1792 NSCLC cell lines harboring the KRAS G12C mutation.

TABLE 1

| Cell lines (KRAS mutation) | $IC_{50}$s (nM) | | |
|---|---|---|---|
| | Compound 1 | AMG-510 | AMG-510 + Compound 1 (1 μM) |
| H358 (G12C) | 2500 | 213 | 3 |
| H23 (G12C) | 4059 | >10000 | ~1500 |
| H2122 (G12C) | 1936 | 530.3 | 90.5 |
| H1373 (G12C) | ~5000 | >10000 | 355.7 |
| H1792 (G12C) | 1901 | >10000 | ~3000 |

Results showing cell viability % of the KRAS G12C inhibitor MRTX849, Compound 1, and the combination of the KRAS inhibitor MRTX849 with Compound 1 (1 μM) in KRAS G12C mutated H358, and H2122 cells were also determined. We investigated the effect of Compound 1(1 μM) in combination with MRTX849 on cell proliferation in H358 and H2122 NSCLC cell lines with KRAS G12C mutation. Compound 1 at 1 μM concentration shifted MRTX849's $IC_{50}$ from 75 nM to 11 nM against H358 cell proliferation and from 182 nM to 42 nM against H2122 cell proliferation.

Results showing cell viability % of the KRAS G12C inhibitor ARS-1620, Compound 1, and the combination of the KRAS inhibitor ARS-1620 with Compound 1(1 μM) in KRAS G12C mutated H358, and H2122 cells were determined. We investigated the effect of Compound 1(1 μM) in combination with ARS-1620 on cell proliferation in H358 and H2122 NSCLC cell lines with KRAS G12C mutation. Compound 1 at 1 μM concentration shifted ARS-1620's $IC_{50}$ from 488 nM to 88 nM against H358 cell proliferation and from 1287 nM to 52 nM against H2122 cell proliferation.

Example 2: Apoptosis Assays

Two thousand cells per well were seeded in 384 well white plate, and then treated with compounds for 24 or 48 hours (37° C., 5% $CO_2$). Cell caspase-3/7 activity, a major hallmark of apoptosis, was measured using Caspase-Glo® 3/7 detection assay (Promega) following the manufactures's protocol. Results showing the increase of caspase-3/7 activity with 24 and 48 hour treatments of AMG510 (50 nM), Compound 1 (1 μM), and the combination of AMG510 (50 nM) with Compound 1(1 μM) in NSCLC cell lines harboring a KRAS G12C mutation (H358, H2122, H1373) are shown in FIG. 1a-1f. Compound 1 alone increased caspase-3/7 activity in H358 and H2122 NSCLC cell lines (FIGS. 1a-1d). AMG510 alone increased caspase-3/7 activity with H358, H2122, and H1373 NSCLC cell lines (FIGS. 1a-1f). The combination of Compound 1 with AMG510 caused more caspase-3/7 activation compared to AMG510 treatment alone for NSCLC cells with a G12C mutation (FIGS. 1a-1f) at both 24 and 48 hour timepoints.

Cleaved PARP and cleaved caspase-3 were evaluated as biomarkers of apoptosis. Half a million cells per well were seeded in 24 well plate for 24 hrs, and then treated with compounds for 4, 24 or 48 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, IX Halt protease and phosphatase inhibitors (Thermo Scientific). Protein lysates (approximately 20 μg) was resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting PARP, Cleaved caspase-3, tubulin and actin (Cell Signaling Technology). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). Results in the H358 KRAS G12C NSCLC cell line demonstrated large increases in cleaved PARP and cleaved caspase-3 after both 24 and 48 hour treatments with the combination of AMG510 (100 nM) and Compound 1 (1 μM). Treatment with AMG510 alone (100 nM) or Compound 1 alone (1 μM) resulted in small increases in cleaved PARP and cleaved caspase-3 protein. Activation of apoptosis was demonstrated by cleaved PARP and cleaved caspase-3 in H358 mutant KRAS G12C NSCLC cells after 24 hr or 48 hr with AMG510 (100 nM), Compound 1 (1 μM), and the combination of AMG510 (100 nM) and Compound 1 (1 μM) after 48 hrs. Results in H2122 KRAS G12C NSCLC demonstrated large increases in cleaved PARP and cleaved caspase-3 after 48 hour treatment with the combination of AMG510 (100 nM) and Compound 1 (1 μM). Treatment with AMG510 (100 nM) alone or Compound 1 (1 μM) alone had minimal-to-no increases in increased cleaved PARP and cleaved caspase-3 which was strikingly less than the combination of Compound 1 and AMG510. The activation of apoptosis was also demonstrated by cleaved PARP and cleaved caspase-3 in H2122 mutant KRAS G12C NSCLC cells after 48 hour treatment with AMG510 (100 nM), Compound 1 (1 μM), and the combination of AMG510 (100 nM) and Compound 1 (1 μM).

Example 3. Immunoblotting for Cellular Kinase Phosphorylation Assays

Half a million cells per well were seeded in 6 well or 24 well plate for 24 hrs, and then treated with compounds for 4, 24 or 48 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, IX Halt protease and phosphatase inhibitors (Thermo Scientific). Protein lysates (approximately 20 μg) was resolved on 4-12% Bolt Bis-Tris pre-casted gels with MES running buffer (Life Technologies), transferred to nitrocellulose membranes using Trans-Blot Turbo Transfer System (Bio-Rad) and detected with antibodies targeting phosphorylated STAT3, FAK, SRC, HER2, AKT, ERK, S6 (Cell Signaling Technology), total STAT3, FAK, SRC, HER2, AKT, S6 ERK and cleaved caspase 3 (Cell Signaling Technology). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). The inhibition of phosphorylation of STAT3, ERK, AKT, and FAK by Compound 1 (1 μM), AMG510 (100 nM), and Compound 1 (1 μM)+ AMG510 (100 nM) was measured after 4, 24, and 48 hrs.

Results in H358 KRAS G12C NSCLC showed that Compound 1 alone suppressed protein levels of phospho-STAT3 (pSTAT3), phospho-FAK (pFAK) at 4, 24 and 48 h time points. AMG510 did not suppress pSTAT3 or pFAK protein levels at any time point. The combination of Compound 1 and AMG510 suppressed pFAK and pSTAT3 protein levels at all time points. Compound 1 alone did not suppress phospho-ERK (pERK) at any time point. AMG510 did not suppress pERK at 4 hours of treatment but does after 24 and 48 hours of treatment. The combination of Compound 1 with AMG510 suppressed pERK at all timepoints. Treatment with Compound 1 alone or AMG510 alone had minimal-to-no suppression of phospho-AKT (pAKT) with treatments up to 24 hours. Treatment of 48 hours with AMG510 alone increased pAKT while 48 treatment with Compound 1 alone decrease pAKT relative to control. The combination of Compound 1 with AMG510 had significant suppression of pAKT after 24 and 48 hours of treatment, which support the significantly increased activation of apoptosis in the combination treatment.

The inhibition of phosphorylation of FAK, STAT3, SRC, HER2, ERK, AKT, and S6 and the activation of apoptosis by cleaved caspase-3 by Compound 1 (1 μM), MRTX849 (100 nM), and Compound 1 (1 μM)+MRTX849 (100 nM) was evaluated in H2122 mutant KRAS G12C NSCLC cells after 4 hrs, 24 hrs and 48 hrs. Results in H2122 KRAS G12C NSCLC show that Compound 1 alone suppressed protein levels of phospho-STAT3 (pSTAT3), phospho-FAK (pFAK) and phospho-SRC at 4, 24 and 48 h time points. MRTX849 did not suppress pSTAT3, pFAK or pSRC protein levels at any time point. The combination of Compound 1 and MRTX849 suppressed pFAK, pSTAT3 and pSRC protein levels at all time points. Compound 1 alone did not suppress phospho-ERK (pERK) at any time point while MRTX849 suppresses pERK at all time points. The combination of Compound 1 with MRTX849 suppressed pERK at all timepoints. Treatment with Compound 1 alone or MRTX849 alone suppressed phospho-AKT (pAKT) at all time points. Treatment of 48 hours with MRTX849 alone increased pHER2. The combination of Compound 1 with MRTX849 had enhanced suppression of pAKT and p-S6 after 4, 24 and 48 hours of treatment than either agent alone and suppressed pHER2 at 48 hours which support the significantly increased activation of apoptosis as demonstrated by cleaved caspase-3 in the combination treatment.

The inhibition of phosphorylation of FAK, STAT3, SRC, ERK, AKT, and S6 by Compound 1 (1 μM), ARS1620 (1 μM), and Compound 1 (1 μM)+ARS1620 (1 μM) was evaluated in H358 mutant KRAS G12C NSCLC cells after 4 hrs, 24 hrs and 48 hrs. Results in H358 KRAS G12C NSCLC show that Compound 1 alone suppressed protein levels of phospho-STAT3 (pSTAT3), phospho-FAK (pFAK) and phospho-SRC at 4, 24 and 48 h time points. ARS1620 did not suppress pSTAT3, pFAK or pSRC protein levels at any time point. The combination of Compound 1 and ARS1620 suppressed pFAK, pSTAT3 and pSRC protein levels at all time points. The combination of Compound 1 with ARS1620 suppressed pERK at all timepoints. Treatment with Compound 1 alone or ARS1620 alone suppressed phospho-AKT (pAKT) with treatments up to 24 hours. Treatment of 48 hours with ARS1620 alone increased pAKT while 48 treatment with Compound 1 alone decrease pAKT relative to control. The combination of Compound 1 with ARS1620 had significant suppression of pAKT and p-S6.

Results in H2122 KRAS G12C NSCLC show that Compound 1 alone suppressed protein levels of phospho-STAT3 (pSTAT3), phospho-FAK (pFAK) and phospho-SRC at 4, 24 and 48 h time points. ARS1620 did not suppress pSTAT3, pFAK or pSRC protein levels at any time point. The combination of Compound 1 and ARS1620 suppressed pFAK, pSTAT3 and pSRC protein levels at all time points. Compound 1 alone did not suppress phospho-ERK (pERK) at any time point while ARS1620 suppressed pERK at 4 and 24 hours. The combination of Compound 1 with ARS1620 suppressed pERK at at 4 and 24 hours. Treatment with Compound 1 alone or ARS1620 alone suppressed phospho-AKT (pAKT) at all time points. The combination of Compound 1 with ARS1620 showed significant enhanced suppression of pAKT and p-S6 than ARS1620 treatment alone.

Example 4: H2122 NSCLC KRAS G12C 2D Assay

H2122 NSCLC cells were used to identify synergistic combinations between AMG-510 or MRTX-849 and Compound 1. One 96-well plate was seeded with 2000 cells/well in a total volume of 80 μl of RPMI supplemented with 10% fetal bovine serum (FBS). The following day, a combination matrix was generated comprising a horizontally diluted drug titration of AMG-510 or MRTX-849 (final concentration of 10 μM diluted 3-fold down to 1.5 nM) with a vertically titrated Compound 1 (final concentration of 3 μM to 37 nM diluted 3 fold). The cells were incubated for 96 hours at 37 C in 5% $CO_2$. Subsequently, 36 μl of Cell-Titer Glo reagent (Promega) was added to each well and the plates were incubated for 10 min at 37 C. Luminescence was quantitated using a Synergy H1 microplate plate reader (Biotek) according to the manufacturer's instructions. Synergy was assessed by BLISS independence analysis on the Synergyfinder website (Ianevski A, He L, Aittokallio T, Tang J. SynergyFinder: a web application for analyzing drug combination dose-response matrix data. Bioinformatics. 2017 Aug. 1; 33(15): 2413-2415).

Figure 2B:
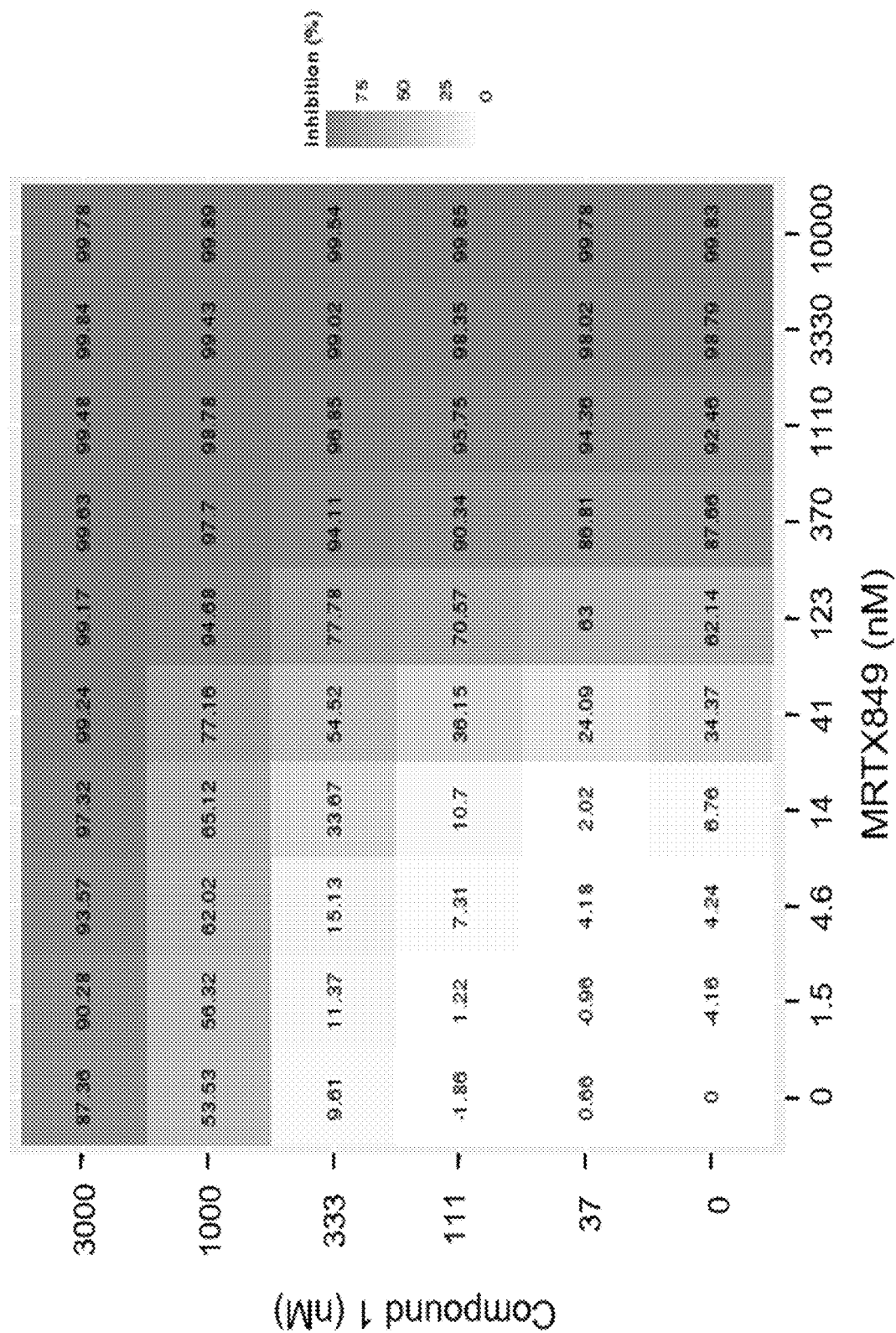
FIG. 2b is a chart showing the 2D dose response matrix after treatment of H2122 cells with a compound 1 and KRAS inhibitor MRTX849 at various concentrations from 0 nM to 3000 nM of Compound 1, and from 0 nM to 10000 nM KRAS inhibitor MRTX849.

In the in vitro combination screen, KRAS inhibitors (AMG-510 and MRTX-849) and Compound 1 demonstrated synergy in H2122 cells. A visualization of the dose response matrix are shown in FIGS. 2a-2b. Table 2 shows the Bliss synergy scores for relevant drug doses.

TABLE 2

|  | Compound 1 | BLISS Synergy Score |
| --- | --- | --- |
| AMG-510 |  |  |
| 41 nM | 1000 nM | 21 |
| 123 nM | 1000 nM | 16 |
| MRTX-849 |  |  |
| 41 nM | 1000 nM | 7 |
| 123 nM | 1000 nM | 12 |

Example 5: Compound 1 and Combinations with AMG510 Alter Secretion of Cytokines and Growth Factors from Mutant KRAS Tumor Cells Cytokines and Growth Factors Evaluated ENA-78 (CXCL5), GCSF, GM-CSF, GRO alpha/beta/gamma, GRO alpha (CXCL1), I-309 (TCA-3/CCL1), IL-1 alpha (IL-1 F1), IL-1 beta (IL-1 F2), IL-2, IL-3, IL-4, IL-5, IL-6, IL-7, IL-8 (CXCL8), IL-10, IL-12 p40/p70, IL-13, IL-15, IFN-gamma, MCP-1 (CCL2), MCP-2 (CCL8), MCP-3 (MARC/CCL7), M-CSF, MDC (CCL22), MIG (CXCL9), MIP-1 beta (CCL4), MIP-1 delta (CCL15), RANTES (CCL5), SCF, SDF-1 alpha (CXCL12 alpha), TARC (CCL17), TGF beta 1, TNF alpha, TNF beta (TNFSF1B), EGF, IGF1, Angiogenin, Oncostatin M, Thrombopoietin (TPO), VEGF-A, PDGF-BB, Leptin, BDNF, BLC (CXCL13), Ckbeta 8-1 (CCL23), Eotaxin-1 (CCL11), Eotaxin-2 (MPIF-2/CCL24), Eotaxin-3 (CCL26), FGF-4, FGF-6, FGF-7 (KGF), FGF-9, Flt-3 Ligand, Fractalkine (CX3CL1), GCP-2 (CXCL6), GDNF, HGF, IGFBP-1, IGFBP-2, IGFBP-3, IGFBP-4, IL-16, IP-10 (CXCL10), LIF, Light (TNFSF14), MCP-4 (CCL13), MIF, MIP-3 alpha (CCL20), NAP-2 (PPBP/CXCL7), NT-3, NT-4, Osteopontin (SPP1), Osteoprotegerin (TNFRSF11B), PARC (CCL18), PLGF, TGF beta 2, TGF beta 3, TIMP-1, TEMP-2.

Experimental Method

Cytokine Array

Cytokines present in NCI-H358 and NCI-H2122 conditioned media were identified and quantitatively compared using Human Cytokine Antibody Array C5 (AAH-CYT-5-8, RayBiotech). One million cells per well were seeded in 6 well plates and allowed to attach for 24 h, and then treated with AMG-510 (100 nM)/MRTX849 (100 nM), Compound 1 (1 μM) or the combination of AMG-510 (100 nM)/MRTX849 (100 nM) and Compound 1 (1 μM) for 24 or 48 hours. Antibody arrays were blocked for 30 minutes at room temperature, following incubation with conditioned media from H358 and H2122 cells overnight at 4° C. Antibody arrays were then washed and re-incubated with the biotinylated antibody cocktail overnight at 4° C., followed with HRP-conjugated streptavidin for 2 h at room temperature. Following a final wash step, chemiluminescence detection buffers were added to arrays and chemiluminescence signals were captured using a iBright 1500 imaging system (Invitrogen). The spot density was quantified by using the iBright Analysis Software and compared using the RayBiotech Analysis tool for AAH-CYT-5.

ELISA

Half a million cells per well were seeded in 6 well plates and allowed to attach for 24 hrs, and then treated with AMG-510 (100 nM)/MRTX849 (100 nM), Compound 1 (1 μM) or the combination of AMG-510 (100 nM)/MRTX849 (100 nM) and Compound 1 (1 μM) for 48 hours. To assess IL-6 secretion by tumor cells, supernatants were harvested and human IL-6 ELISA assays were performed per manufacturer's instructions (R&D Biosystems). Briefly, microplate wells were incubated with either the standard, control and sample supernatants from H358 and H2122 cells for 2 hours at room temperature. Microplates were then washed and incubated with human IL-6 conjugate for 2 hours at room temperature, followed by washing and addition of substrate solution for 20 minutes. Finally stop solution is added and optical density evaluated using a microplate reader set to 450 nm. Readings at 540 nm were substracted to correct for optical imperfections in the plate.

qPCR

Half a million cells per well were seeded in 6 well plates and allowed to attach for 24 hrs, and then treated with AMG-510 (100 nM)/MRTX849 (100 nM), Compound 1 (1 μM) or the combination of AMG-510 (100 nM)/MRTX849 (100 nM) and Compound 1 (1 μM) for 24 and 48 hours. mRNA was prepared using the Rneasy Mini Kit (Qiagen) and cDNA synthesized using Superscript IV VILO (Invitrogen). qPCR was carried out with diluted cDNA, appropriate Taqman probes and Taqman Fast Advanced Master mix (Applied Biosystems) using a QuantStudio 5 Thermal Cycler (Applied Biosystems). Relative mRNA levels were calculated using the 2-Ct method, using RPL32 as an internal control.

KRAS cell lines H358 and H2122 shown to secrete IL-6, and IL-6 is shown to be inhibited by Compound 1 alone and in the presence of AMG510, where the inhibition of IL-6 secretion is greater in the combination of Compound 1 and AMG-510, than with either compound individually. Results are shown in FIGS. 3a-3d.

Figure 3A:
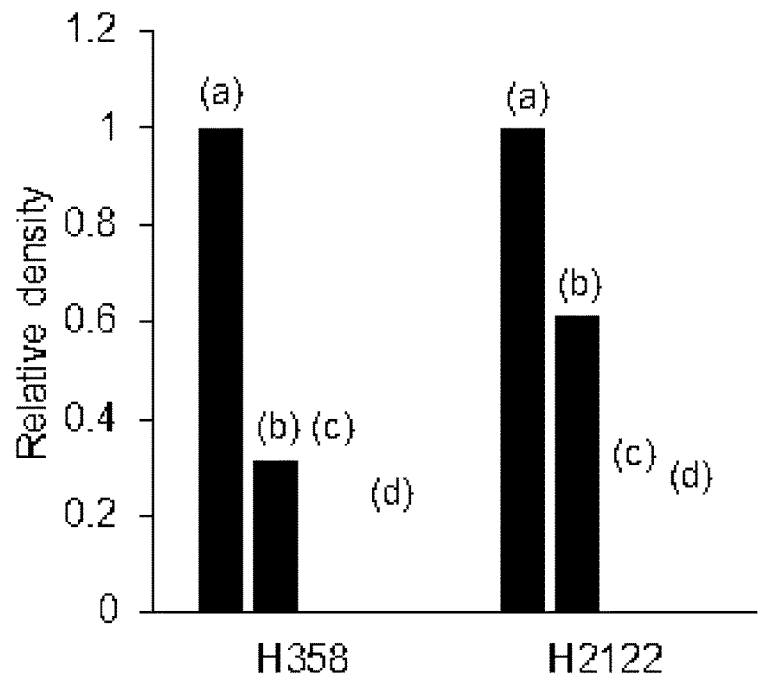
FIG. 3a is a graph showing decreased IL-6 secretion in H358 and H2122 NSCLC cell lines treated for 48 h with a combination of Compound 1 with AMG-510. (a) Control; (b) AMG-510; (c) Compound 1; (d) Compound 1+AMG-510.
Figure 3B:
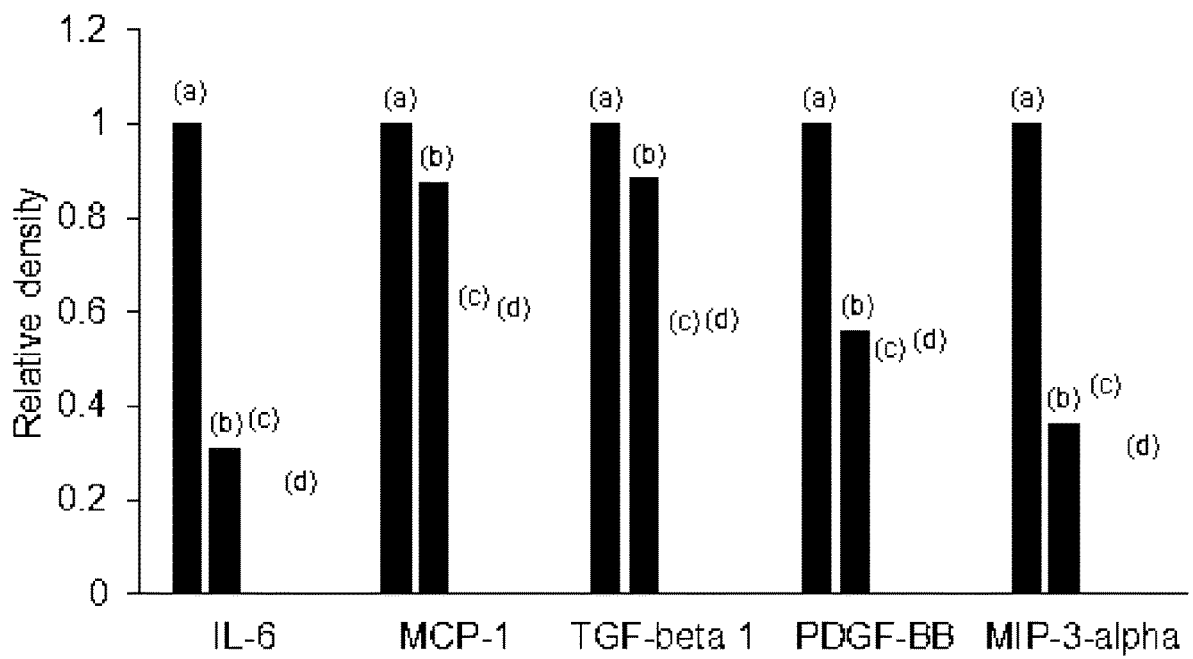
FIG. 3b is a chart showing decreased secretion of IL-6, MCP-1, TGF-β1, PDGF-BB, and MIP-3-alpha in H358 cells treated with the combination of Compound 1 and AMG-510 for 48 h. (a) Control; (b) AMG-510; (c) Compound 1; (d) Compound 1+AMG-510.
Figure 3C:
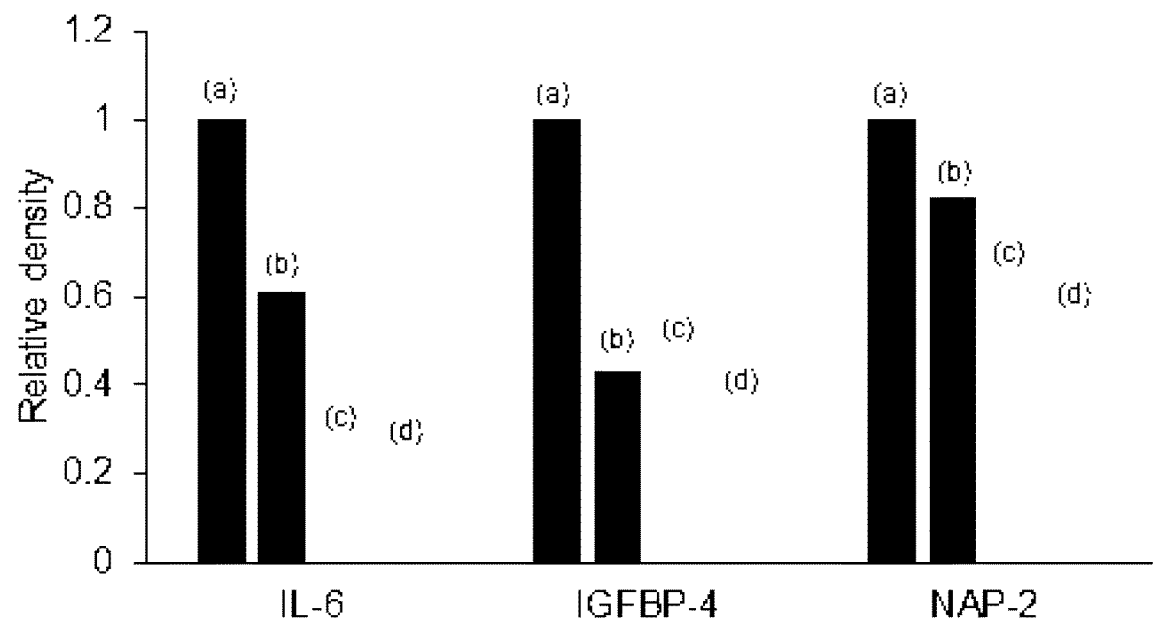
FIG. 3c is a chart showing decreased secretion of IL-6, IGFBP-4 and NAP-2 in H2122 cells treated with the combination of Compound 1 and AMG-510 for 48 h. (a) Control; (b) AMG-510; (c) Compound 1; (d) Compound 1+AMG-510.
Figure 3D:
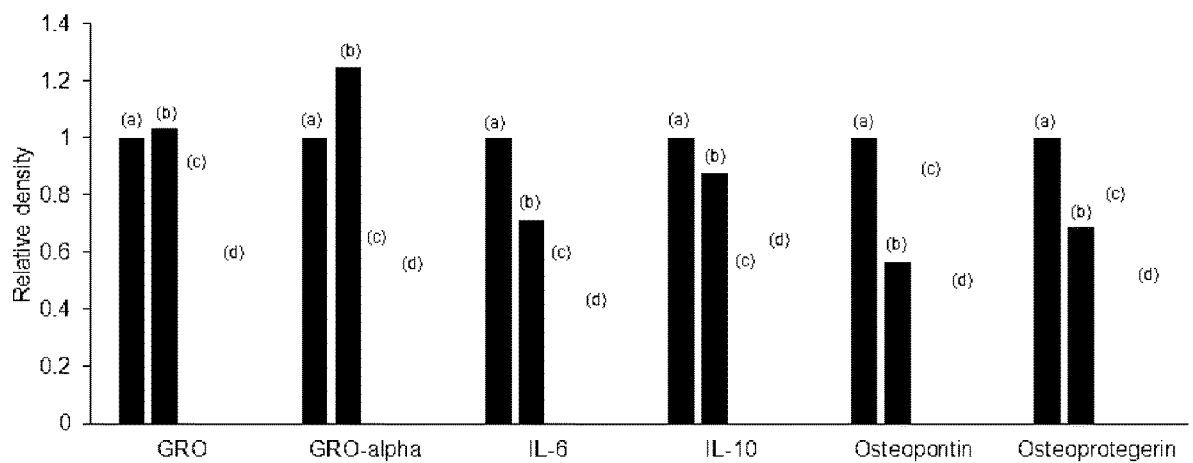
FIG. 3d is a chart showing decreased secretion of IL-6, GRO, GRO-alpha, IL-10, osteopontin, and osteoprotegerin in H358 cells treated with the combination of Compound 1 and AMG-510 for 24 h. (a) Control; (b) AMG-510; (c) Compound 1; (d) Compound 1+AMG-510.
Figure 3E:
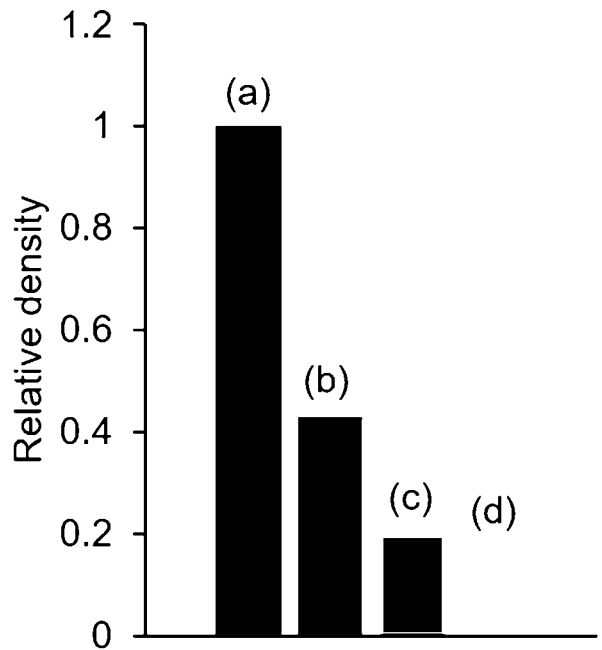
FIG. 3e is a graph showing decreased IL-6 secretion in H2122 NSCLC cell lines treated for 48 h with a combination of Compound 1 with MRTX849. (a) Control; (b) MRTX849; (c) Compound 1; (d) Compound 1+MRTX849.

Cytokine data was also generated in H2122 NSCLC cell lines treated for 48 h with a combination of Compound 1 with MRTX849. (a) Control; (b) MRTX849; (c) Compound 1; (d) Compound 1+MRTX849 (FIG. 3e).

Figure 3F:
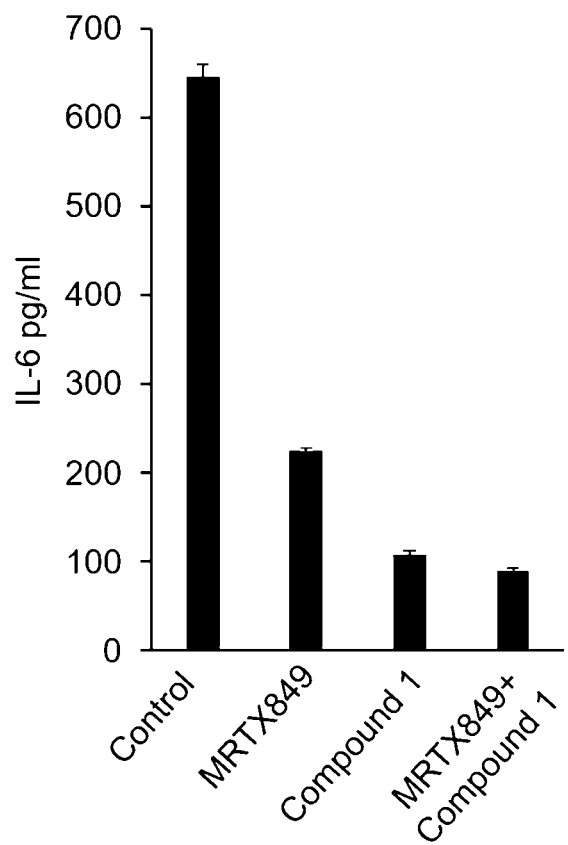
FIG. 3f is an ELISA assay showing decreased IL-6 secretion in H2122 NSCLC cell lines treated for 48 h with a combination of Compound 1 with MRTX849.

KRAS cell line H2122 shown to secrete IL-6, and IL-6 is shown to be inhibited by Compound 1 alone and in the presence of MRTX849, where the inhibition of IL-6 secretion is greater in the combination of Compound 1 and MRTX849, than with either compound individually (FIGS. 3f-3g).

In-Vivo Studies

Method 1: Subcutaneous Xenograft Models in Immune Compromised Mice

Female athymic nude, SCID, NOD/SCID or SCID/Beige mice (5-8 weeks of age) were used as host mice. For subcutaneous cell-derived xenograft models, about five million cells in 100 μL serum-free medium supplemented with 50% matrigel (Corning, Inc) were implanted subcutaneously in the right flank region of each host mouse. For subcutaneous patient-derived xenograft models, a tumor fragment from host mice was implanted subcutaneously in the flank region of each host mouse. Tumor size and body weight were measured on designated days. Tumor size was measured with an electronic caliper and tumor volume was calculated as the product of length*width$^2$*0.5 or similar formula. Mice were randomized by tumor size into treatment groups when mean tumor volume reached a certain size. Compound 1 was administered orally twice a day at determined doses and AMG-510 was administered orally once a day at determined doses. For brain orthotopic models, about 80000 cells were implanted into brain and treatment of mice with control or test articles started 7 days post the implantation.

Method 2: Tumor Processing and Immunoblotting for In Vivo Pharmacodynamic Studies Mice bearing xenograft tumors were humanely euthanized and tumors were resected and snap frozen in liquid nitrogen and stored at −80° C. Frozen tumor samples were processed at 4° C. in RIPA buffer to extract proteins. Protein concentration of the lysate was determined by Rapid Gold BCA Protein Assay (Life Technologies, Inc.) and lysate were diluted to ensure the same protein concentration across samples. SDS loading samples were prepared by adding one volume of 4×LDS Sample Buffer (Life Technologies, Inc.) to three volumes of diluted protein lysate. Tumor SDS protein samples were processed by SDS-PAGE and immunoblotted appropriate primary antibodies, followed by detection using HRP conjugated secondary antibodies. The signals from immunoblot were detected by C-DiGit Blot Scanner from LI-COR using the Image Studio Digit software (LI-COR).

Figure 4A:
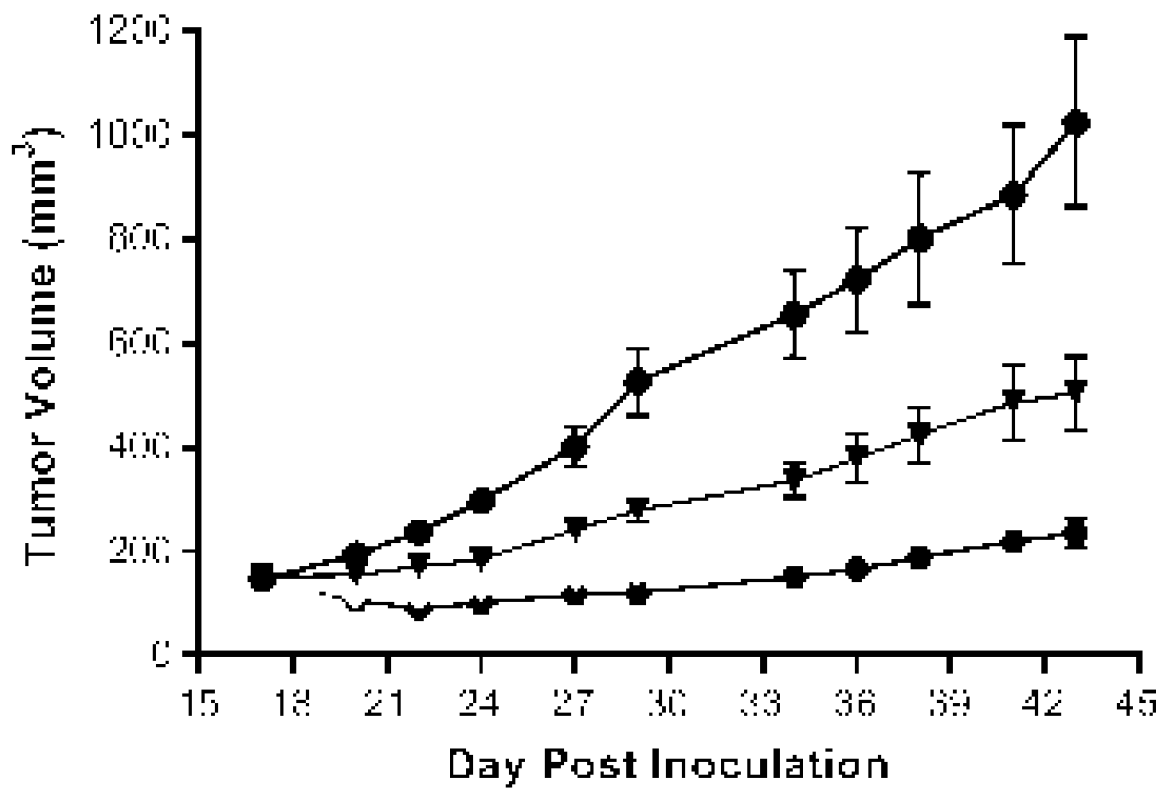
FIG. 4a is a chart showing the antitumor effect of Compound 1 in combination with AMG-510 in H358 cell-derived xenograft tumors harboring a KRAS G12C mutation. (•) Control; (▼) Compound 1 (15 mg/kg BID); (♦) AMG-510 (10 mg/kg QD); (•) Compound 1 (15 mg/kg BID) plus AMG-510 (10 mg/kg QD).
Figure 4B:
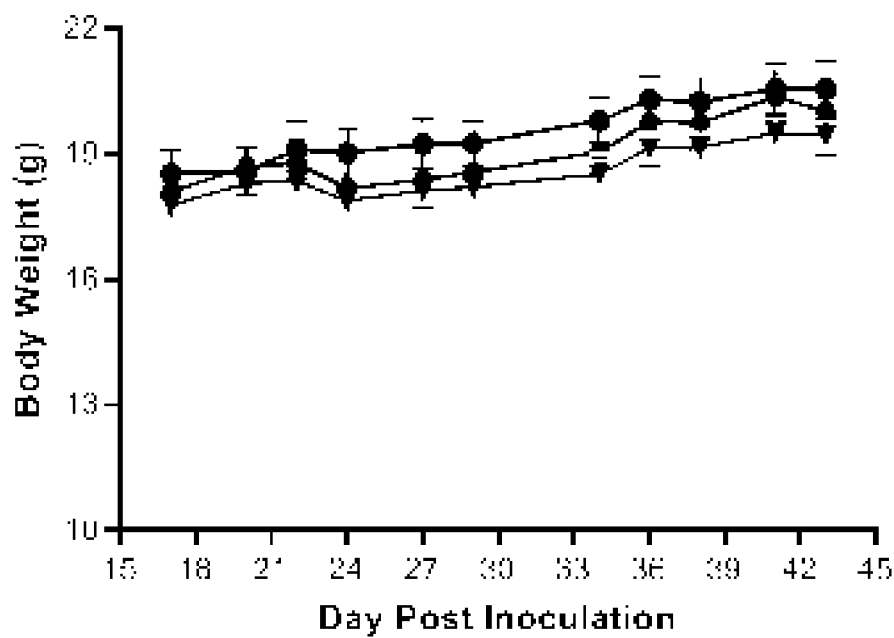
FIG. 4b is a chart showing the body weight of mice bearing H358 cell-derived tumors harboring a KRAS G12C mutation when treated with Compound 1 in combination with AMG-510. (•) Control; (▼) Compound 1 (15 mg/kg BID); (♦) AMG-510 (10 mg/kg QD); (•) Compound 1 (15 mg/kg BID) plus AMG-510 (10 mg/kg QD).

Example 6: Effect of Compound 1 in Combination with AMG-510 in H358 Cell-Derived Xenograft Tumors H358 cells harbor a KRAS G12C mutation. SCID/Beige mice bearing H358 cell-derived tumors were treated with vehicle BID, Compound 1 BID at 15 mg/kg, AMG-510 QD at 10 mg/kg, and Compound 1 BID at 15 mg/kg in combination with AMG-510 QD at 10 mg/kg, respectively. The tumor volume (TMV) vs time data are shown as mean±sem in FIG. 4a. After 26 days of treatment, Compound 1 in combination with AMG-510 significantly reduced tumor volume compared to the treatment with vehicle, Compound 1 only or AMG-510 only ($p<0.0001$ for all three comparisons, post hoc Tukey's multiple comparison test following two-way repeated measures ANOVA analysis). Body weight of the mice were measured during treatment and are shown as mean±sem in FIG. 4b. There is no statistical significance among treatment groups ($p=0.4233$, two-way repeated measures ANOVA), suggesting that the combination treatment of Compound 1 and AMG-510 did not resulted in any body weight loss or overt abnormality under these experimental conditions.

Example 7: Pharmacodynamic Effect of Compound 1 in Combination with AMG510 in H358 Cell-Derived Xenograft Tumors To evaluate the pharmacodynamic effect of Compound 1 in combination with AMG-510 in H358 cell-derived xenograft tumors, tumor lysate was prepared and analyzed by immunoblotting using antibodies against the candidate molecules selected from signaling pathways that can be potentially modified by Compound 1 and/or AMG-510. The inhibitory activities of Compound 1 against SRC and JAK2 were demonstrated by the reduction of phosphorylated SRC (Y416) and STAT3 (Y705) signals in tumors treated by Compound 1 either as the single agent or in combination with AMG-510, compared to vehicle treatment. In addition, the activity of Compound 1 against FAK was shown by the reduced the phosphorylated FAK signal in Compound 1 and AMG-510 combination treatment group. Moreover, the AMG-510 activity against KRAS was illustrated by the reduced level of phosphorylated ERK (T202/Y204) signal, a key downstream effector of KRAS signaling in mice treated by AMG-510 either as a single agent or in combination with Compound 1. Finally, combination of Compound 1 with AMG-510 also reduced the phosphorylated AKT (S473) signal, a key factor involved in cell survival and proliferation. Therefore, Compound 1 and AMG-510 combinatory treatment not only Compound 1 and AMG-510 targets, including SRC, FAK, JAK2, and KRAS, but also suppress the activity of AKT, a key factor for the PI3K-AKT oncogenic pathway.

Figure 5A:
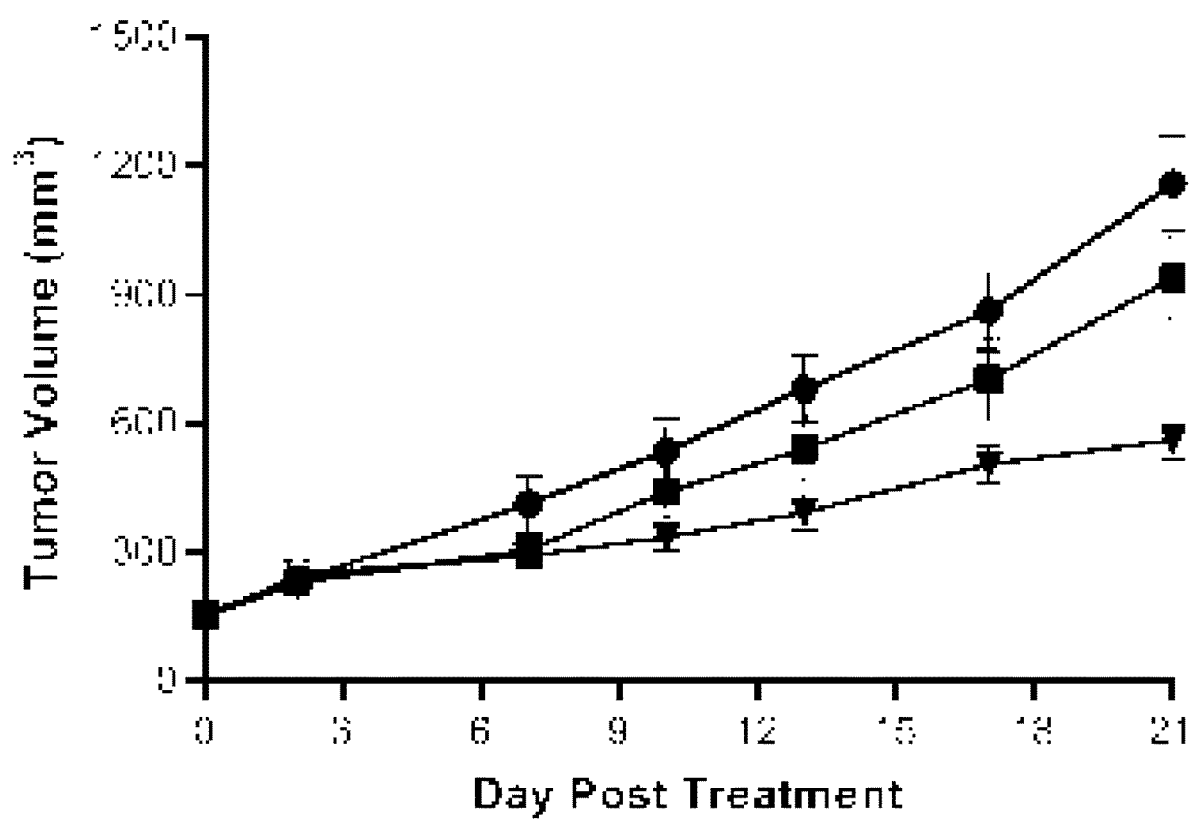
FIG. 5a is a chart showing the antitumor effect of Compound 1 in combination with AMG-510 in LU11693 PDX model harboring a KRAS G12C mutation. The dose of AMG-510 was reduced to 30 mg/kg QD after 14 days of treatment. Two mice in the combination treatment group terminated on day 13. (•) Control; (■) Compound 1 (15 mg/kg BID); (▲) AMG-510 (100 mg/kg QD); (▼) Compound 1 (15 mg/kg BID) plus AMG-510 (100 mg/kg QD).
Figure 5B:
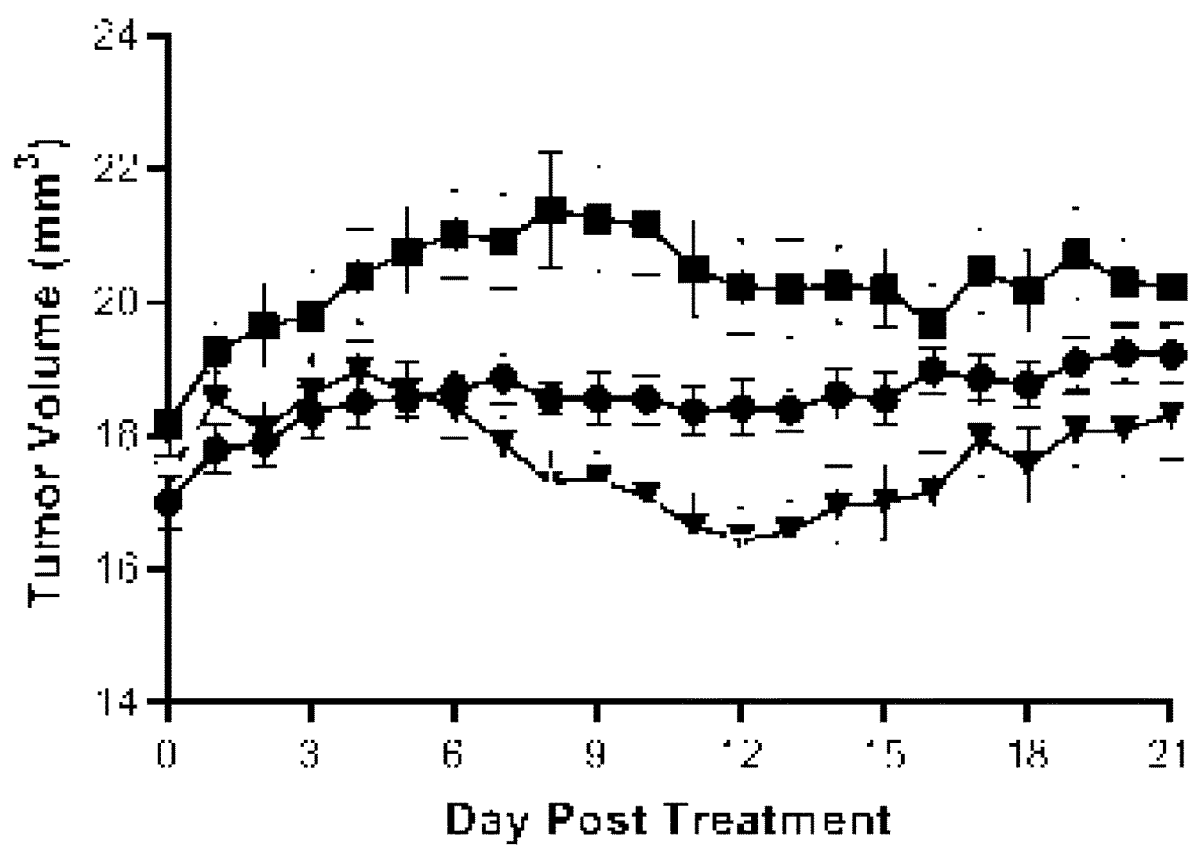
FIG. 5b is a chart showing the body weight of mice bearing LU11693 PDX harboring a KRAS G12C mutation when treated with Compound 1 in combination with AMG-510. The dose of AMG-510 was reduced to 30 mg/kg QD after 14 days of treatment. Two mice in the combination treatment group terminated on day 13. (•) Control; (■) Compound 1 (15 mg/kg BID); (▲) AMG-510 (100 mg/kg QD); (▼) Compound 1 (15 mg/kg BID) plus AMG-510 (100 mg/kg QD).

Example 8: Effect of Compound 1 in Combination with AMG-510 in LU11693 Patient-Derived Xenograft Model of NSCLC Harboring a KRAS G12C Mutation LU11693 PDX tumors harbor a KRAS G12C mutation. NOD/SCID mice bearing LU11693 PDX tumors were treated with vehicle BID, Compound 1 BID at 15 mg/kg, AMG-510 QD at 100 mg/kg, and Compound 1 BID at 15 mg/kg in combination with AMG-510 QD at 100 mg/kg, respectively. The tumor volume vs time data are shown as mean±sem in FIG. 5a. Body weight of the mice were measured during treatment and are shown as mean±sem in FIG. 5b. Treatment with AMG-510 at 100 mg/kg QD either as a single agent or in combination with Compound 1 significantly reduced body weight of mice. On day 13, two mice in the combination treatment groups were euthanized due to the loss of body weight and the dose of AMG-510 was reduced to 30 mg/kg QD starting on day 14 in both AMG-510 only treatment and the Compound 1 and AMG-510 combination treatments. After 21 days of treatment, Compound 1 in combination with AMG-510 significantly reduced tumor volume compared to the treatment compared to the treatment with vehicle, Compound 1 only or AMG-510 only ($p=0.0002$ vs vehicle, $p=0.0181$ vs Compound 1, $p=0.0003$ vs AMG-510, post hoc Dunnett's multiple comparison test following mixed-effect model). As stated above, body weight loss was observed in mice treated with AMG-510 at 100 mg/kg QD either as a single agent or in combination with Compound 1. After dose reduction, the body weight in the Compound 1 plus AMG-510 combination group start to recover and, on day 21, the body weight in the combination group is not significant different from the vehicle treated group (p=0.5487 vs vehicle, Dunnett's multiple comparisons test following one-way ANOVA).

Example 9: Improvement of Survival of Mice Bearing H2122 Cell-Derived Xenograft Tumors by Compound 1 in Combination with AMG-510

Figure 6A:
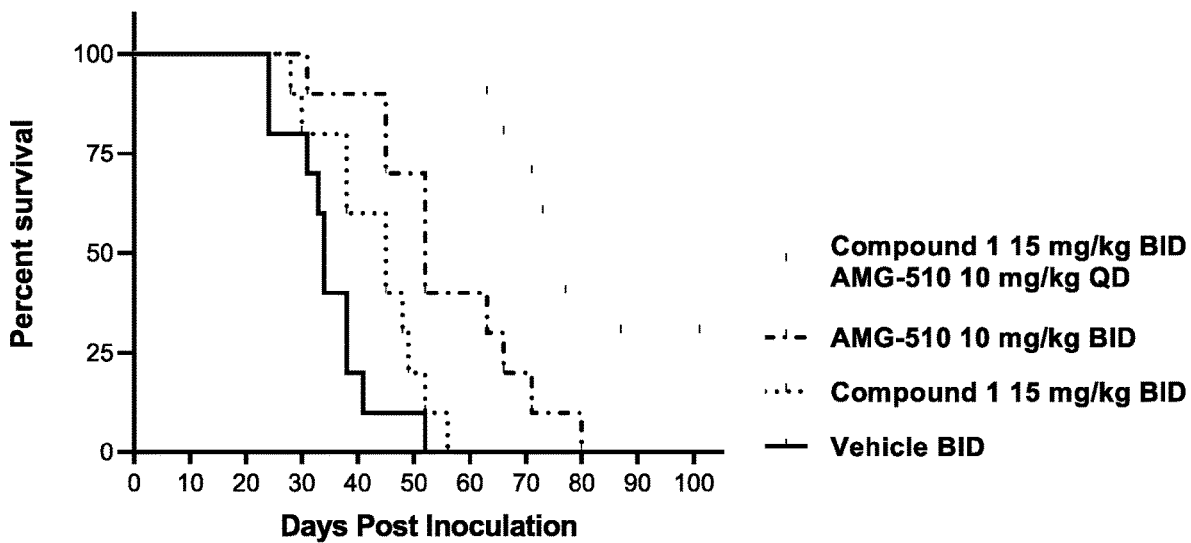
FIG. 6a is a chart showing the effect of Compound 1 in combination with AMG-510 on survival in H2122 cell-derived xenograft tumor model harboring a KRAS G12C mutation. The dose level of AMG-510 was at 10 mg/kg QD. (__) Control; (...) Compound 1 (15 mg/kg BID); (_..) AMG-510 (10 mg/kg QD); (_ _) Compound 1 (15 mg/kg BID) plus AMG-510 (10 mg/kg QD).
Figure 6B:
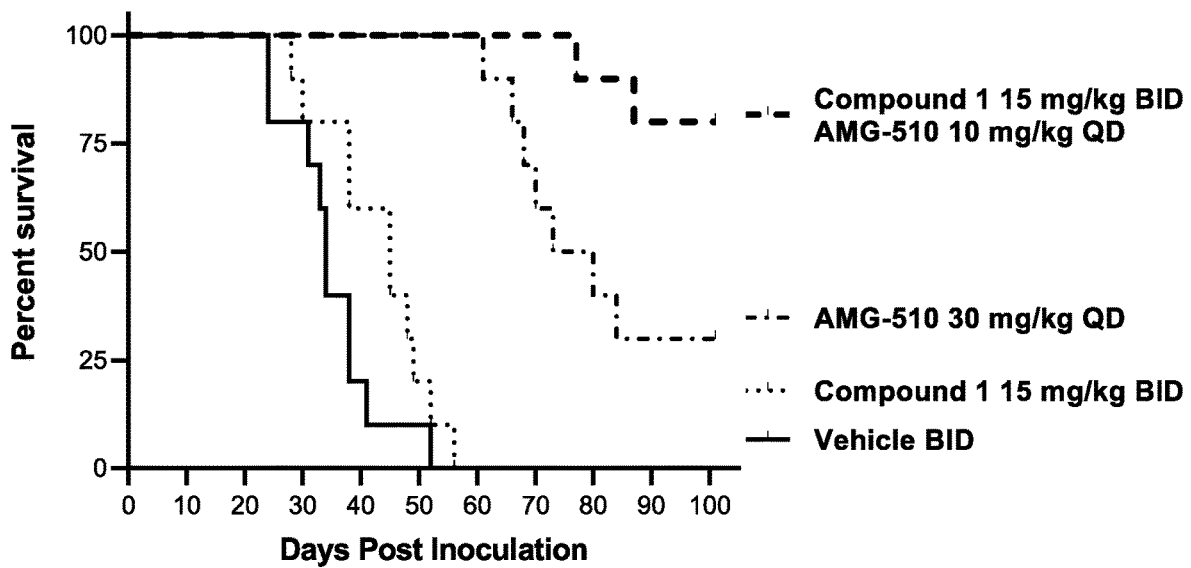
FIG. 6b is a chart showing the effect of Compound 1 in combination with AMG-510 on survival in H2122 cell-derived xenograft tumor model harboring a KRAS G12C mutation. The dose level of AMG-510 was at 30 mg/kg QD. (_) Control; (...) Compound 1 (15 mg/kg BID); (_.) AMG-510 (30 mg/kg QD); (_ _) Compound 1 (15 mg/kg BID) plus AMG-510 (30 mg/kg QD).

The effect of Compound 1 and AMG-510 combination treatment on survival of tumor bearing mice was evaluated using the H2122 cell-derived xenograft tumor model with the $KRAS^{G12C}$ mutation. Starting on day 5 post tumor cell implantation, SCID/Beige mice bearing H2122 cell-derived xenograft tumors were randomized in to groups (n=10 for each group) based on tumor size and treated with vehicle BID, Compound 1 BID at 15 mg/kg, AMG-510 QD at 10 mg/kg, Compound 1 BID at 15 mg/kg in combination with AMG-510 QD at 10 mg/kg, AMG-510 QD at 30 mg/kg, and Compound 1 BID at 15 mg/kg in combination with AMG-510 QD at 30 mg/kg, respectively. To evaluate the survial effect, individual mouse was considered dead if it reached one of the humane end points: moribund status, tumor volume over 2000 mm$^3$, more than 20% body weight loss compared to baseline, open tumor lesions, and inability to eat or drink. The study ended on day 101 post tumor cell implantation. The median survival were 34, 45, 52, 77, and 76.5 days for the groups treated with vehicle BID, Compound 1 BID at 15 mg/kg, AMG-510 QD at 10 mg/kg, Compound 1 BID at 15 mg/kg in combination with AMG-510 QD at 10 mg/kg, and AMG-510 QD at 30 mg/kg, respectively; and the median survival was not reached for the group treated with Compound 1 BID at 15 mg/kg in combination with AMG-510 QD at 30 mg/kg when the study was terminated on day 101 post the tumor cell implantation. At 10 mg/kg dose level of AMG-510, treatment with Compound 1 in combination with AMG-510 statistically significantly increased the median survival compared to the treatment with AMG-510 only (p<0.0019, Log-rank test, Compound 1 and AMG-510 combination vs AMG-510, FIG. 6a). At 30 mg/kg dose level of AMG-510, treatment with Compound 1 in combination with AMG-510 statistically significantly increased the median survival compared to the treatment with AMG-510 only (p<0.0138, Log-rank test, Compound 1 and AMG-510 combination vs AMG-510, FIG. 6b). These findings suggest that combination treatment of Compound 1 and AMG-510 prolonged the survival of the mice bearing H2122 cell-derived tumors compared to AMG-510 single agent treatment.

The invention claimed is:
1. A method for treating a cancer having a KRAS G12C mutation in a human patient in need thereof, the method comprising the step of administering to the human patient a therapeutically effective amount of a compound that inhibits FAK, SRC, and JAK2, in combination with a therapeutically effective amount of at least one agent that inhibits KRAS G12C, wherein the compound has the structure:

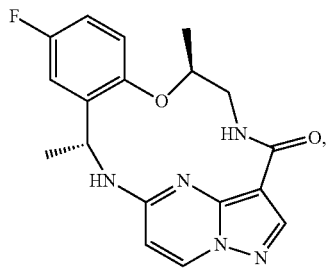 [SMILES: C[C@H]1CNC(=O)c2cnn3ccc(nc23)N[C@H](C)c2cc(F)ccc2O1]

or a pharmaceutically acceptable salt thereof,
the at least one agent that inhibits KRAS G12C is AMG-510, MRTX849, or ARS-1620, or a pharmaceutically acceptable salt thereof; and
the cancer is colorectal cancer, pancreatic cancer, or lung cancer.

2. The method of claim 1, wherein the cancer is pancreatic cancer.

3. The method of claim 1, wherein the cancer is lung cancer.

4. The method of claim 3, wherein the cancer is non-small cell lung cancer.

5. The method of claim 1, wherein the cancer is colorectal cancer.

6. The method of claim 1, wherein the compound that inhibits FAK, SRC, and JAK2 is administered at the same time as, before, or after the at least one agent that inhibits KRAS G12C.

7. The method of claim 1, wherein IL-6 secretion from the cancer is decreased.

8. The method of claim 1, wherein the at least one agent that inhibits KRAS G12C is ARS-1620, or a pharmaceutically acceptable salt thereof.

9. The method of claim 1, wherein the at least one agent that inhibits KRAS G12C is AMG-510, or a pharmaceutically acceptable salt thereof.

10. The method of claim 1, wherein the at least one agent that inhibits KRAS G12C is MRTX849, or a pharmaceutically acceptable salt thereof.

11. The method of claim 1, wherein the compound that inhibits FAK, SRC and JAK2 is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

12. The method of claim 1, wherein the compound that inhibits FAK, SRC and JAK2 is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

13. The method of claim 1, wherein the human patient has not received a prior treatment.

14. The method of claim 1, wherein the human patient has received at least one prior treatment of one or more chemotherapeutic agents or immunotherapies.

15. The method of claim 1, wherein the human patient in has received at least one prior treatment of one or more chemotherapeutic agents or immunotherapies, and developed an acquired resistance to the treatment, and/or developed bypass resistance to the treatment, and/or developed bypass resistance to the treatment regulated by FAK, SRC or JAK2.

16. A method for treating a cancer having a KRAS G12C mutation in a human patient in need thereof, the method comprising the step of administering to the human patient a therapeutically effective amount of a compound that inhibits FAK, SRC, and JAK2, in combination with a therapeutically effective amount of at least one agent that inhibits KRAS G12C, wherein the compound has the structure:

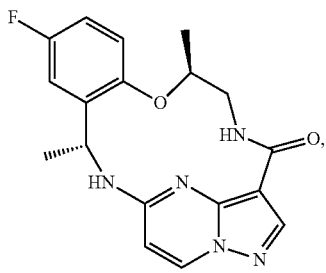 [SMILES: C[C@H]1CNC(=O)c2cnn3ccc(nc23)N[C@H](C)c2cc(F)ccc2O1]

the at least one agent that inhibits KRAS G12C is AMG-510, MRTX849, or ARS-1620, or a pharmaceutically acceptable salt thereof; and the cancer is colorectal cancer, pancreatic cancer, or lung cancer.

17. The method of claim 16, wherein the cancer is pancreatic cancer.

18. The method of claim 16, wherein the cancer is lung cancer.

19. The method of claim 18, wherein the cancer is non-small cell lung cancer.

20. The method of claim 16, wherein the cancer is colorectal cancer.

21. The method of claim 16, wherein the compound that inhibits FAK, SRC, and JAK2 is administered at the same time as, before, or after the at least one agent that inhibits KRAS G12C.

22. The method of claim 16, wherein IL-6 secretion from the cancer is decreased.

23. The method of claim 16, wherein the at least one agent that inhibits KRAS G12C is ARS-1620, or a pharmaceutically acceptable salt thereof.

24. The method of claim 16, wherein the at least one agent that inhibits KRAS G12C is AMG-510, or a pharmaceutically acceptable salt thereof.

25. The method of claim 16, wherein the at least one agent that inhibits KRAS G12C is MRTX849, or a pharmaceutically acceptable salt thereof.

26. The method of claim 16, wherein the compound that inhibits FAK, SRC and JAK2 is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 100 mg to about 300 mg, or about 160 mg; and the at least one agent that inhibits KRAS G12C is administered at a dose of about 0.1 mg to about 3 g, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g, or about 800 mg to about 1.5 g, or at least 800 mg, or at least 600 mg, or about 960 mg, or about 600 mg.

27. The method of claim 16, wherein the compound that inhibits FAK, SRC and JAK2 is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg and the at least one agent that inhibits KRAS G12C is administered at a dose of about 0.1 mg/kg to about 1 g/kg, or about 0.5 mg/kg to about 50 mg/kg, or about 0.5 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg, or about 1.25 mg/kg to about 3.75 mg/kg, or about 1.0 mg/kg, about 2.0 mg/kg, or about 3.0 mg/kg, or about 4.0 mg/kg.

28. The method of claim 16, wherein the human patient has not received a prior treatment.

29. The method of claim 16, wherein the human patient has received at least one prior treatment of one or more chemotherapeutic agents or immunotherapies.

30. The method of claim 16, wherein the human patient has received at least one prior treatment of one or more chemotherapeutic agents or immunotherapies, and developed an acquired resistance to the treatment, and/or developed bypass resistance to the treatment, and/or developed bypass resistance to the treatment regulated by FAK, SRC or JAK2.

* * * * *